(12) United States Patent
Hatala et al.

(10) Patent No.: US 8,362,234 B2
(45) Date of Patent: Jan. 29, 2013

(54) SOLID SUPPORT REAGENTS FOR SYNTHESIS

(75) Inventors: Paul J. Hatala, Charlestown, MA (US); Markus Kurz, Basel (CH)

(73) Assignee: Archemix LLC

( * ) Notice: Subject to any disclaimer, the term of this patent is extended or adjusted under 35 U.S.C. 154(b) by 688 days.

(21) Appl. No.: 12/225,568

(22) PCT Filed: Mar. 26, 2007

(86) PCT No.: PCT/US2007/007751
§ 371 (c)(1),
(2), (4) Date: Oct. 14, 2009

(87) PCT Pub. No.: WO2007/126941
PCT Pub. Date: Nov. 8, 2007

(65) Prior Publication Data
US 2010/0041866 A1 Feb. 18, 2010

Related U.S. Application Data

(60) Provisional application No. 60/785,838, filed on Mar. 24, 2006.

(51) Int. Cl.
*C07H 21/00* (2006.01)
*C07C 63/04* (2006.01)
*C07D 209/46* (2006.01)
*C07D 209/48* (2006.01)

(52) U.S. Cl. ................ 536/25.32; 539/25.34; 548/472; 548/473; 562/493

(58) Field of Classification Search .................. None
See application file for complete search history.

(56) References Cited

U.S. PATENT DOCUMENTS

| | | | |
|---|---|---|---|
| 4,415,732 A | 11/1983 | Caruthers et al. | 536/27 |
| 4,458,066 A | 7/1984 | Caruthers et al. | 536/27 |
| 4,500,707 A | 2/1985 | Caruthers et al. | 536/27 |
| 4,668,777 A | 5/1987 | Caruthers et al. | 536/27 |
| 4,725,677 A | 2/1988 | Köster et al. | 536/27 |
| 4,973,679 A | 11/1990 | Caruthers et al. | 536/27 |
| 5,132,418 A | 7/1992 | Caruthers et al. | 536/27 |
| RE34,069 E | 9/1992 | Köster et al. | 536/27 |
| 5,419,966 A | 5/1995 | Reed et al. | 428/406 |
| 5,869,579 A | 2/1999 | Hodges et al. | |
| 2005/0182241 A1 | 8/2005 | Ngo et al. | |

OTHER PUBLICATIONS

Agrawal et al., "Efficient methods for attaching non-radioactive labels to the 5' ends of synthetic oligodeoxyribonucleotides", *Nucl. Acids Res.*, 14(15):6227-6245 (1986).
Alul et al., "Oxalyl-CPG: A labile support for synthesis of sensitive oligonucleotide derivatives", *Nucl. Acids Res.*, 19:1527-1532 (1991).
Asseline et al., "Nucleic acid-binding molecules with high affinity and base sequence specificity; Intercalating agents covalently linked to oligodeoxynucleotides", *Proc. Natl. Acad. Sci.*, 81:3297-3301 (1984).
Cahn et al., "Specification of Molecular Chirality", *Agnew. Chem. Inter. Edit.*, 5(4):385-415 (1966).
Connell et al., "Automated DNA Sequence Analysis", *BioTechniques*, 5(4):342-348 (1987).
Connolly, "The synthesis of oligonucleotides containing a primary amino group at the 5'-terminus", *Nucl. Acids Res.*, 15(7):3131-3139 (1987).
Letsinger et al., "Cholesteryl-conjugated oligonucleotides: Synthesis, properties, and activity as inhibitors of replication of human immunodeficiency virus in cell culture", *Proc. Natl. Acad. Sci.*, 86:6553-6556 (1989).
Nelson et al., "A new and versatile reagent for incorporating multiple primary aliphatic amines into synthetic oligonucleotides", *Nucl. Acids Res.*, 17(18):7179-7186 (1989).
Petrie et al., "An Improved CPG Support for the Synthesis of 3'-Amine-Tailed Oligonucleotides", *Bioconj. Chem.* 3:85-87 (1992).
Sinha et al., "The preparation and application of functionalized synthetic oligonucleotides: III. Use of H-phosphonate derivatives of protected amino-hexanol and mercapto-propanol or -hexanol", *Nucl. Acids Res.*, 16(6):2659-2669 (1988).
Smith et al., "The synthesis of oligonucleotides containing an aliphatic amino group at the 5' terminus: synthesis of fluorescent DNA primers for use in DNA sequence analysis", *Nucl. Acids Res.*, 13(7):2399-2412 (1985).
Sproat et al., "The synthesis of protected 5'-amino-2',5'-dideoxyribonucleoside-3'-0-phosphoramidites; applications of 5'-amino-oligodeoxyribonucleotides", *Nucl. Acids Res.*, 15:6181-6196 (1987).
Wachter et al., "A simple and efficient procedure for the synthesis of 5'-aminoalkyl oligodeoxynucleotides", 14(20):7985-7994 (1986).
Wright et al., "Large Scale Synthesis of Oligonucleotides via Phosphoramidite Nucleosides and a High-loaded Polystyrene Support", *Tetrahedron Letters*, 34:3373-3376 (1993).
Azhayev et al. "Advancements in Oligonucleotide Synthesis." *Genetic Engineering News* 25.5 (Mar. 1, 2005).

*Primary Examiner* — Lawrence E Crane

(74) *Attorney, Agent, or Firm* — Mintz Levin Cohn Ferris Glovsky and Popeo, P.C.; Ivor R. Elrifi; Jennifer A. Karnakis, Esq.

(57) ABSTRACT

The present invention relates to a compound according to the formula:

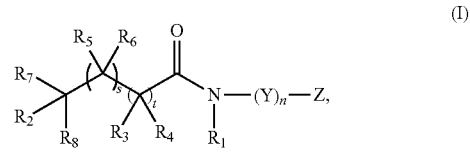

(I)

wherein $R_1$, $R_2$, $R_3$, $R_4$, $R_5$, $R_6$, $R_7$, $R_8$, Y, Z, n, s, and t are as defined herein. These compounds are useful for methods of solid phase synthesis.

19 Claims, 1 Drawing Sheet

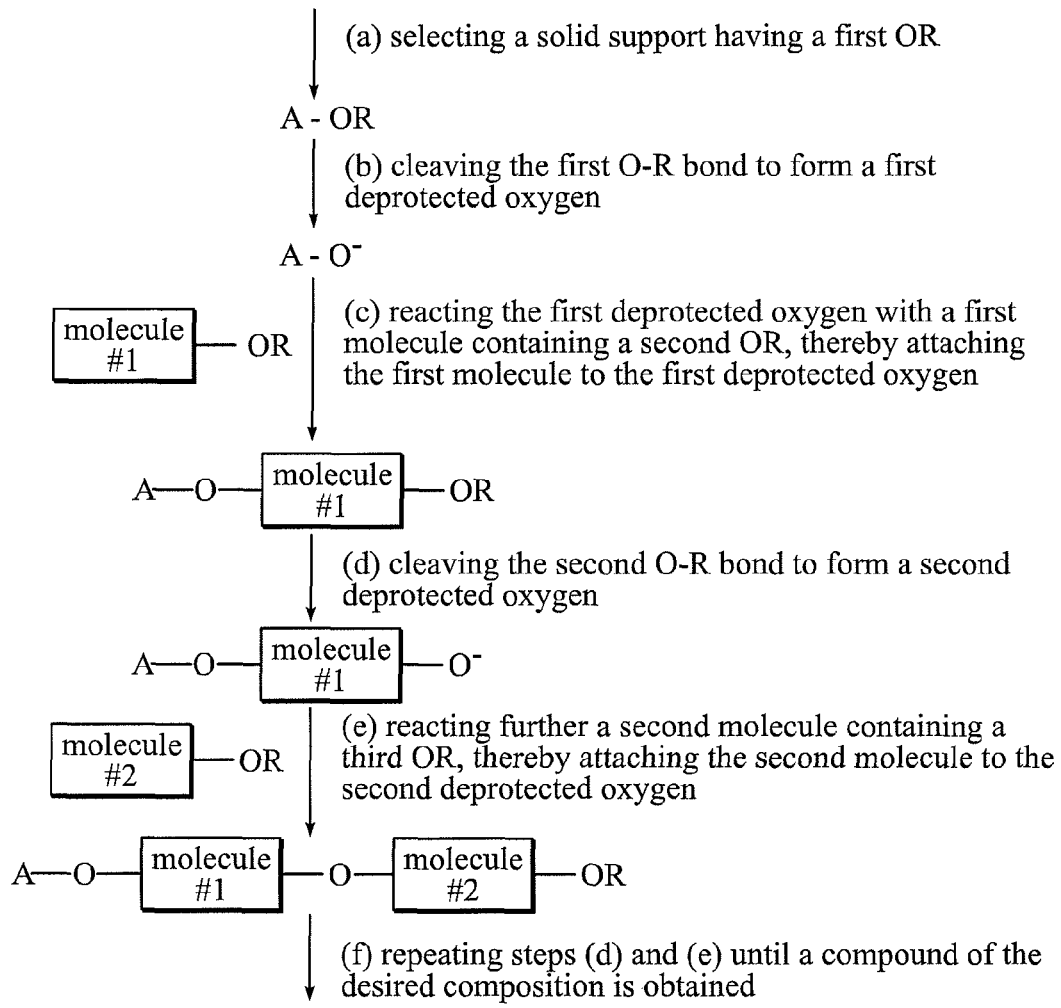

SOLID SUPPORT REAGENTS FOR SYNTHESIS

RELATED APPLICATIONS

This patent application is a national stage application, filed under 35 U.S.C. §371, of International Application No. PCT/US2007/007751, filed on Mar. 26, 2007, which claims the benefit of and priority to U.S. Provisional Patent Application Ser. No. 60/785,838, filed Mar. 24, 2006, which is herein incorporated by reference in its entirety.

FIELD OF THE INVENTION

This invention relates generally to compounds and their use as solid support reagents for methods of solid phase synthesis.

BACKGROUND OF THE INVENTION

This invention relates to solid support reagents useful for synthesis. In recent years, solid phase synthesis has emerged as a powerful tool in high throughput synthesis for the preparation of small molecule libraries and oligomeric materials such as oligonucleotides, peptides, and carbohydrates. More particularly, this invention is directed to solid support reagents and methods of synthesizing oligonucleotides having a modified 3'-terminus.

Current methods to introduce chemical modifications into oligonucleotides employ special phosphoramidite reagents during solid phase synthesis. The primary aliphatic amine group is one of the most widely used chemical modifications since it reacts with many commercially available labeling reagents. Attention has focused on modification of the 5' terminus and a number of protected amino-alkyl phosphoramidites have been reported to incorporate an amino group into the 5' position of oligonucleotides. Agrawal, S., (1986) Nucl. Acids. Res. 14, 6115; Connolly, B. A., (1987), Nucl. Acids Res. 15, 3131; Jablonski, E., (1987) Nucl. Acids Res. 15, 5275; Smith, L. M., (1985) Nucl. Acids Res. 13, 2399; Connell, C., (1987) BioTechniques 5, 342; Sproat, B. S., (1987) Nucl. Acids Res. 15, 6181; Sinha, N. D. (1988) Nucleic Acids Res. 16, 2659. Oligonucleotides modified by these reagents can be subsequently derivatized with fluorophores, biotin, and other molecules.

It is also well-known that the usefulness of oligonucleotides can be enhanced by modification at the 3'-terminus e.g., by including small molecular weight groups at the 3'-end such as the 3'-tailed cholesterol oligonucleotides of Letsinger et al. used to inhibit HIV-1 replication (Proc. Natl. Acad. Sci. 86:6553-6556 (1989)) and 3'-tailed acridine oligonucleotides of Asseline et al. found to be stabilized intercalating agents which improved binding to complementary sequences (Proc. Natl. Acad. Sci. 81:8297-3301 (1984)). The stability of 3'-modified oligonucleotides in serum may also be enhanced. For example, unmodified oligonucleotides are rapidly degraded by 3' exonucleases in serum containing media.

Techniques to prepare oligonucleotides with a modified 3' terminus are less convenient and more tedious than the better known methods to prepare 5' modified oligonucleotides. Thus, useful synthetic methods for the synthesis of 3'-substituted oligonucleotides have been slower to develop. Nelson et al. Nuc. Acids Res. 17:7179 (1989) has described a phosphoramidite reagent which he states can be incorporated at any position in the synthetic oligonucleotide. However, Nelson has only demonstrated the use of this reagent to incorporate a primary aliphatic amine on the 5'-terminus of an oligonucleotide sequence. Nelson et al. Nuc. Acids Res. 17:7187 (1989) has also described the synthesis of a multi-functional controlled pore glass (CPG) which can be used to incorporate 3' terminal primary aliphatic amines into synthetic oligonucleotides. This reagent known as Amine-On CPG (Clontech) is commercially available but has been reported to give unpredictable results (See, Petrie, et al. Bioconj. Chem. 3:85 (1992)).

Petrie et al. Bioconj. Chem. 3:85 (1992) has reported an improved CPG support for the synthesis of 3'-amino substituted oligonucleotides. This support, 3'-aminohexyl CPG (AH-CPG), allows for the direct synthesis of oligonucleotides bearing a 3'-aminohexyl substituent. Petrie utilized the AH-CPG support to prepare an 11-mer oligonucleotide and showed it to be a distinct product by both polyacrylamide gel electrophoresis and reversed-phase HPLC. This AH-CPG method suffers from both slow cleavage from the solid support and amino group deprotection, which thereby limits the type of oligonucleotides that can be synthesized and often limits yield.

Reed et al. U.S. Pat. No. 5,419,966 has also reported a controlled pore glass matrix (CPG) support for oligonucleotide synthesis which has the following structure:

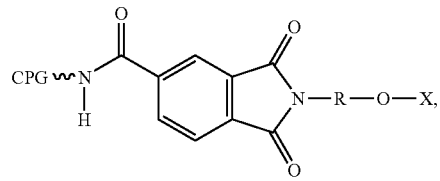

where 1,3-dioxoisoindoline-5-carboxamide serves as a linking group between the CPG support and the oligonucleotide chain. The wavy line represents a carbon chain which covalently links the NH group of the carboxamide with the controlled pore glass matrix, X is 2,2'-dimethyoxytrityl or H, and R is alkyl, aryl, arylalkyl, heteroalkyl, or heteroaryl. The dimethoxytrityl group is removed from the CPG support by treatment with acid, and the oligonucleotide is built, step-by-step, in a conventional synthesizer after attachment of the 3' end of the first oligonucleotide unit to the hydroxyl function connected to the R group. Because methods to prepare oligonucleotides with a modified 3' terminus are inconvenient and more tedious, useful synthetic methods for the synthesis of 3'-substituted oligonucleotides have been slow to develop. Accordingly, there is a clear need for improved methods to prepare oligonucleotides with a modified 3' terminus.

SUMMARY OF THE INVENTION

The invention includes compounds which can be attached to a solid support and used as a reagent for methods of solid phase synthesis. In one aspect, the invention includes a compound of Formula I:

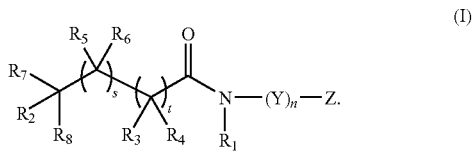

$R_1$ is selected from hydrogen and $C_1$-$C_6$ alkyl. $R_2$ is selected from hydrogen, hydroxy, and $C_1$-$C_6$ alkoxy, or together $R_1$ and $R_2$ form a single bond. $R_3$, $R_4$, $R_5$, and $R_6$ are the same or different from each other and each represents hydrogen, $C_1$-$C_6$ alkyl, and halogen, or together $R_3$ and $R_4$ with $R_5$ and $R_6$ form an aromatic ring, further wherein the aromatic ring is substituted with one or more X. X is selected from halogen, nitro, amino, and aminocarbonyl. The letter "s" represents 0, 1, 2, or 3. The letter "t" represents 0, 1, 2, or 3, provided that s+t≧1. $R_7$ and $R_8$ are the same or different from each other and each represents hydroxy, halogen, hydrogen, $C_1$-$C_6$ alkoxy, oxyacyl, or together $R_7$ and $R_8$ form a carbonyl. Y is selected from a methylene or substituted methylene, nucleoside, nucleotide, protected nucleoside, protected nucleotide, $C_5$-$C_8$ aryl, arylalkyl, heteroalkyl, heterocycle, and heteroaryl. In one embodiment, Y is methylene or substituted methylene. The letter "n" determines the number of Y and is selected from 1, 2, 3, 4, 5, 6, 7, 8, 9, or 10. Z is selected from OR and NHR. R is selected from hydrogen, $SiR^aR^bR^c$, $CR^aR^bR^c$, heteroalkyl, and $C_1$-$C_6$ alkyl. $R^a$, $R^b$, and $R^c$ are the same as or different from each other and each represents methyl, ethyl, i-propyl, t-butyl, phenyl or substituted phenyl.

One embodiment of the invention includes the compound of Formula II:

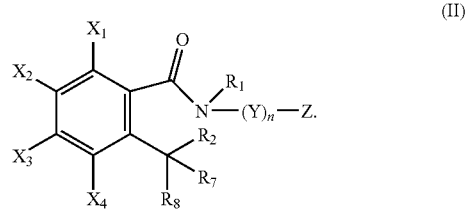

(II)

$R_1$ is selected from hydrogen and $C_1$-$C_6$ alkyl. $R_2$ is selected from hydrogen, hydroxy, oxyacyl, $C_1$-$C_6$ alkoxy, and $C_1$-$C_6$ alkyl, or together $R_1$ and $R_2$ form a single bond. $R_7$ and $R_8$ are each independently selected from hydroxy, halogen, hydrogen, $C_1$-$C_6$ alkoxy, oxyacyl, or together $R_7$ and $R_8$ form a carbonyl. $X_1$, $X_2$, $X_3$, and $X_4$ are selected from hydrogen, halogen, nitro, amino, and aminocarbonyl, provided that at least one of $X_1$, $X_2$, $X_3$, and $X_4$ is not hydrogen. Y is selected from a methylene or substituted methylene, nucleoside, nucleotide, protected nucleoside, protected nucleotide, $C_5$-$C_8$ aryl, arylalkyl, heteroalkyl, heterocycle, and heteroaryl. In one embodiment, Y is selected from methylene or substituted methylene. The letter "n" determines the number of Y and is selected from 1, 2, 3, 4, 5, 6, 7, 8, 9, or 10. Z is selected from OR and NHR. R is selected from hydrogen, $SiR^aR^bR^c$, $CR^aR^bR^c$, heteroalkyl, and $C_1$-$C_6$ alkyl. $R_a$, $R^b$, and $R^c$ are the same as or different from each other and each represents methyl, ethyl, i-propyl, t-butyl, phenyl or substituted phenyl.

In one embodiment of the compound of Formula II, together $R_7$ and $R_1$ form a carbonyl. In another embodiment, together $R_1$ and $R_2$ form a single bond. In another embodiment, $R_1$ is hydrogen. In another embodiment, one of $R_7$ or $R_8$ is $OC(O)CH_3$ and the other is hydrogen. In another embodiment, one of $R_7$ or $R_8$ is hydroxy and the other is hydrogen.

In one aspect, $X_2$ is selected from nitro, —$NH_2$, alkylamino, dialkylamino, and aminocarbonyl. In another aspect, $X_2$ is nitro. In one embodiment, Y is phosphoramidite. In another embodiment, Y is $CH_2$. In another embodiment, n is 6. In one embodiment, Z is OR. In another embodiment, Z is NHR. In a further embodiment, where Z is OR, R is selected from hydrogen, $Si(t\text{-butyl})(CH_3)_2$, or $C(C_6H_5)(4\text{-MeOC}_6H_4)_2$. In another embodiment, where Z is NHR, R is selected from hydrogen, $Si(t\text{-butyl})(CH_3)_2$, or $C(C_6H_5)(4\text{-MeOC}_6H_4)_2$.

In one embodiment, at least one of $X_1$, $X_3$, and $X_4$ is halogen. $X_2$ is nitro or amino. In another embodiment, at least one of $X_1$, $X_3$, and $X_4$ is chlorine. In another embodiment, $X_2$ is nitro or amino.

Another embodiment of the invention includes the compound of Formula III:

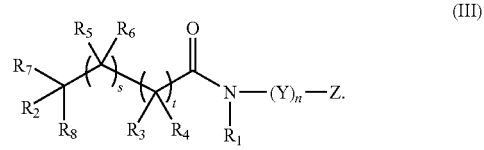

(III)

$R_1$ is selected from hydrogen and $C_1$-$C_6$ alkyl. $R_2$ is selected from hydrogen, hydroxy, $C_1$-$C_6$ alkoxy, and $C_1$-$C_6$ alkyl. $R_3$, $R_4$, $R_5$, and $R_6$ are the same or different from each other and each represents hydrogen, $C_1$-$C_6$ alkyl, or halogen. The letter "s" represents 0, 1, 2, or 3. The letter "t" represents 0, 1, 2, or 3, provided that s+t≧1. $R_7$ and $R_8$ are each independently selected from hydroxy, halogen, hydrogen, $C_1$-$C_6$ alkoxy, oxyacyl, or together $R_7$ and $R_8$ form a carbonyl. Y is selected from a methylene or substituted methylene, nucleoside, nucleotide, protected nucleoside, protected nucleotide, $C_5$-$C_8$ aryl, arylalkyl, heteroalkyl, heterocycle, and heteroaryl. In one embodiment, Y is methylene or substituted methylene. The letter "n" represents 1, 2, 3, 4, 5, 6, 7, 8, 9, or 10. Z is selected from OR and NHR. R is selected from hydrogen, $SiR^aR^bR^c$, $CR^aR^bR^c$, heteroalkyl, and $C_1$-$C_6$ alkyl. $R^a$, $R^b$, and $R^c$ are the same or different from each other and each represents methyl, ethyl, i-propyl, t-butyl, phenyl or substituted phenyl.

In one embodiment of the compound of Formula III, $R_1$ is hydrogen. In another embodiment, $R_2$ is hydroxy. In one embodiment, together $R_7$ and $R_8$ form a carbonyl. In another embodiment, at least one of $R_3$, $R_4$, $R_5$, and $R_6$ is halogen. In another embodiment, at least two of $R_3$, $R_4$, $R_5$, and $R_6$ are halogen. In another embodiment, at least three of $R_3$, $R_4$, $R_5$, and $R_6$ are halogen. In a further embodiment, $R_3$, $R_4$, $R_5$, and $R_6$ are each halogen. In one embodiment, at least one of $R_3$, $R_4$, $R_5$, and $R_6$ is fluorine. In another embodiment, at least two of $R_3$, $R_4$, $R_5$, and $R_6$ are fluorine. In another embodiment, at least three of $R_3$, $R_4$, $R_5$, and $R_6$ are fluorine. In a further embodiment, $R_3$, $R_4$, $R_5$, and $R_6$ are each fluorine.

In one embodiment, Z is hydroxy. In another embodiment, Z is $OSi(t\text{-butyl})(CH_3)_2$. In another embodiment, Z is $OC(C_6H_5)(4\text{-MeOC}_6H_4)_2$. In one embodiment, Y is $CH_2$. In another embodiment, n is 6.

Another embodiment of the invention includes the compound of Formula IV:

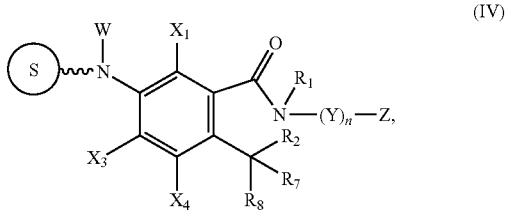

(IV)

where Ⓢ is a solid support. The wavy line ～ represents a carbon chain which optionally contains a carbonyl. W is selected from hydrogen and $C_1$-$C_6$ alkyl. $R_1$ is selected from hydrogen and $C_1$-$C_6$ alkyl. $R_2$ is selected from hydrogen, hydroxy, oxyacyl, $C_1$-$C_6$ alkoxy, and $C_1$-$C_6$ alkyl, or together $R_1$ and $R_2$ form a single bond. $R_7$ and $R_8$ are each independently selected from hydroxy, halogen, hydrogen, $C_1$-$C_6$ alkoxy, oxyacyl, or together $R_7$ and $R_8$ form a carbonyl. $X_1$, $X_3$, and $X_4$ are selected from hydrogen, halogen, nitro, amino and aminocarbonyl. Y is selected from a methylene or substituted methylene, nucleoside, nucleotide, protected nucleoside, protected nucleotide, $C_5$-$C_8$ aryl, arylalkyl, heteroalkyl, heterocycle, and heteroaryl. In one embodiment, the wavy line is an alkyl chain. In another embodiment, the wavy line is a carbonyl e.g.,

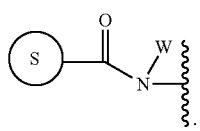

In another embodiment, the wavy line is an alkyl chain containing a carbonyl e.g.,

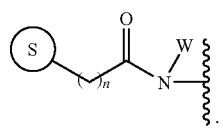

In one embodiment, Y is methylene or substituted methylene. The letter "n" determines the number of Y and is selected from 1, 2, 3, 4, 5, 6, 7, 8, 9, or 10. Z is selected from OR and NHR. R is selected from hydrogen, $SiR^aR^bR^c$, $CR^aR^bR^c$, heteroalkyl, and $C_1$-$C_6$ alkyl. $R^a$, $R^b$, and $R^c$ are the same as or different from each other and each represents methyl, ethyl, i-propyl, t-butyl, phenyl or substituted phenyl.

In one embodiment, the solid support of the compound of Formula IV is selected from controlled pore glass (CPG) or styrene-divinylbenzene (DVB) co-polymer, polyethylene glycol (PEG) or methacrylate based polymers. In another embodiment, the carbonyl in the carbon chain is adjacent to the nitrogen atom on the aromatic ring.

Another embodiment of the invention includes the compound of Formula V:

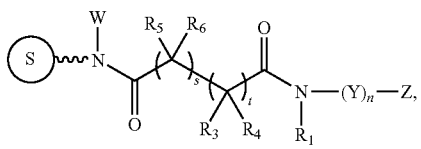

(V)

where Ⓢ is a solid support. The wavy line ∿∿ represents a carbon chain which optionally contains a carbonyl. W is selected from hydrogen and $C_1$-$C_6$ alkyl. $R_1$ is selected from hydrogen and $C_1$-$C_6$ alkyl. $R_3$, $R_4$, $R_5$, and $R_6$ are the same or different from each other and each represents hydrogen, $C_1$-$C_6$ alkyl, or halogen. The letter "s" (where the letter s is not enclosed inside a circle e.g., Ⓢ) is 0, 1, 2, or 3. The letter "t" represents 0, 1, 2, or 3, provided that s+t≦1. Y is selected from a methylene or substituted methylene, nucleoside, nucleotide, protected nucleoside, protected nucleotide, $C_5$-$C_8$ aryl, arylalkyl, heteroalkyl, heterocycle, and heteroaryl. In one embodiment, Y is methylene or substituted methylene. The letter "n" determines the number of Y and is selected from 1, 2, 3, 4, 5, 6, 7, 8, 9, or 10. Z is selected from OR and NHR. R is selected from hydrogen, $SiR^aR^bR^c$, $CR^aR^bR^c$, heteroalkyl, and $C_1$-$C_6$ alkyl. $R^a$, $R^b$, and $R^c$ are the same or different from each other and each represents methyl, ethyl, i-propyl, t-butyl, phenyl or substituted phenyl.

In one embodiment the solid support of the compound is selected from controlled pore glass (CPG) or styrene-divinylbenzene (DVB) co-polymer, polyethylene glycol (PEG) or methacrylate based polymers. In another embodiment, the carbonyl in the carbon chain (represented by the wavy line) is adjacent to the nitrogen atom on the aromatic ring.

The above description sets forth the present invention in order that the detailed description thereof that follows may be understood, and in order that the present contributions of the art may be better appreciated. Other objects and features of the present invention will become apparent from the following detailed description considered in conjunction with the examples.

BRIEF DESCRIPTION OF THE DRAWINGS

FIG. 1 is an illustration depicting the steps of a method of the present invention for synthesizing a compound having a defined composition.

DETAILED DESCRIPTION

The details of one or more embodiments of the invention are set forth in the accompanying description below. Although any methods and materials similar or equivalent to those described herein can be used in the practice or testing of the present invention, the methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present specification will control.

The present invention relates to compounds for use as solid support reagents for the synthesis of small molecules or oligomeric materials such as oligonucleotides, peptides, and carbohydrates. In one aspect of the present invention, it is an objective to provide an improved method of synthesis of oligonucleotides having modified 3' terminus, e.g. an 3'-amino functional group. The solid support reagents of the present invention provide several important advantages over current reagents useful for the synthesis of 3'-amino substituted oligonucleotides. One important advantage of the present invention is shorter cleavage/deprotection times. Once synthesized, the desired 3'-amino oligonucleotide can be cleaved from the solid support reagent of the present invention (i.e. the masked amino group is deprotected to the primary amine and can be disconnected or cleaved from the solid support) substantially faster than that observed using other conventional reagents. For the solid support reagents of the present invention with an aromatic ring, the faster cleavage rate is due to substitution on the aromatic ring with an electron withdrawing group e.g., X is an amine or halogen or in the case of the reagent containing the acetoxy group (e.g.,

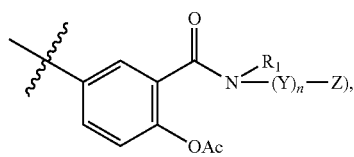

neighboring group participation increases the cleavage rate. For the non-aromatic solid support reagents, the presence of an electron withdrawing group (or groups) such as a halogen increases the cationic character of the adjacent carbonyl group which results in faster attack by nucleophiles. Faster cleavage of oligonucleotides from the solid support is important because it allows for a greater variety of oligonucleotides to be synthesized and obtained in higher yield, with minimal side reactions.

The solid support reagents of the invention are prepared by attaching linking compounds to a solid support typically through a carbon chain linker. The carbon chain linker optionally contains a carbonyl group and the carbon chain linker is represented by a "wavy line" or "∿∿∿". In one embodiment, the carbon chain is an alkyl chain. In another embodiment, the carbon chain is a carbonyl. A "solid support" (also represented as "Ⓢ") is a substrate which is capable of serving as the support in solid phase synthetic methodologies, such as those described in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069. In the present invention, a solid support is the support on which the synthesis takes place. The solid support can have a variety of forms and compositions, however the solid support should (i) be substantially insoluble in the synthesis reagents, (ii) be chemically stable to synthesis reagents, (iii) be capable of chemical derivatization, (iv) be able to provide the desired loading, (v) possess adequate compression strength to withstand elevated pressure encountered during processing, and (vi) be available in a desirable particle size range and distribution.

As used herein, the term "synthesis reagents" refers to solvents and reagents typically used in the synthesis process e.g. reagents used in oligonucleotide synthesis such as iodine, methylene chloride, acetonitrile, toluene, tetrazole and substituted tetazoles, n-methylimidazole, pyridine, carboxcylic anhydrides, lutidine, trifluoroacetic acid or dichloroacetic acid, peroxides and the like.

Solid supports suitable for use in the invention include those generally known in the art to be suitable for use in solid phase methodologies. In one embodiment, the solid support is a polymer. In a further embodiment, the solid support is an inorganic polymer. A wide variety of inorganic polymers can be employed in the present invention and these include, for example, silica, porous glass, aluminosilicates, borosiliates, metal oxides such as alumina and nickel oxide, various clays, and the like. The solid support can be selected from glass, controlled pore glass (CPG), oxalyl-controlled pore glass (see, e.g., Alul, et al., Nucleic Acids Research 1991, 19, 1527), TentaGel Support—an aminopolyethyleneglycol derivatized support (see, e.g., Wright, et al., Tetrahedron Letters 1993, 34, 3373, co-polymers of polystyrene/divinylbenzene e.g., styrene-divinylbenzene (DVB) co-polymer, PEG (polyethylene glycol) or methacrylate based polymers. Methacrylate based polymers are based on the polymerization of methacrolein or methacrolien like molecules and typically a hydroxyl or carboxyl bearing moiety such as oxidized polyethylene. Toyopearl™ and Fractogel® are common examples of methacrylate based polymers.

In one embodiment, the solid support is controlled pore glass (CPG). Controlled pore glass consists of uniformly milled and screened particles of almost pure silica that are honeycombed with pores of a controlled sized. CPG is typically manufactured from a borosilicate material that has been specially heat treated to separate the borates from the silicates. The pores are formed by removing the borates using an acidic etching process, their size being dependent on the nature of the heating process. In one embodiment, the CPG is in the form of 120-200 mesh particles size and having 500-700 angstrom pores. In one embodiment, the CPG is derivatived with a base e.g., an amine. In another embodiment, the CPG may be further functionalized. In one aspect, further functionalization of the CPG is accomplished using amide formatting reaction conditions e.g., carbodiimide coupling reagents such as DCC (1,3-dicyclohexylcarbodiimide) or EDCI (1-(3-dimethylaminopropyl)-3-ethylcarbodiimide hydrochloride). Controlled pore glass beads for use in oligonucleotide synthesis are available from e.g., CPG, Inc., Pierce Chemical Co., Prime Synthesis, Inc., and Sigma Aldrich.

In another embodiment, the solid support is divinylbenzene (DVB) co-polymer. Divinylbenzene co-polymer is a solid support commonly consisting of styrene and divinylbenzene, although other substances such methacrylate can be incorporated. DVB is a common copolymer used extensively in solid supported organic synthesis, solid phase synthesis in general, and as a base for chromatography resins. DVB is supplied by many manufactures including e.g., Merck Gmbh, Rohm and Haas, and Dow. DVB can be funcionalized with many groups including a carboxylic acid, hydroxyl or amino groups. In one aspect, functionalization of DVB is accomplished under amide forming reaction conditions e.g., carbodiimide (DCC or EDCI) coupling conditions.

"Linking compounds" mean the compounds which form a connection between the solid support and the compound of desired composition. The "boxed" areas shown below are examples of linking compounds. The linking compound does not include the solid support, the carbon chain used for attachment to the solid support and represented by the wavy line, or any part of the group Z which includes the compound of a desired composition which has been synthesized.

Linking Compounds

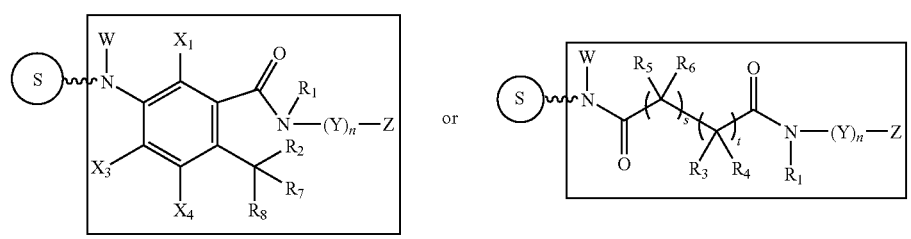

In one embodiment, the linking compound serves to mask the 3'-terminal nitrogen of the synthetic oligonucleotide and to connect the synthetic oligonucleotide to the solid support. Another purpose of the linking compound is to provide appropriate spacing between the solid support and the molecule being synthesized in order to reduce the extent to which the solid support interferes with the synthesis of the molecule.

In one embodiment of the invention, the linking compound refers to a compound of the Formula I:

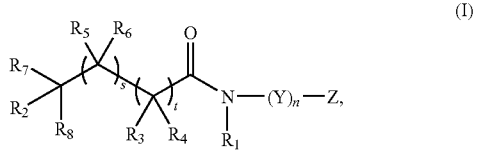

(I)

where $R_1$ is selected from hydrogen and $C_1$-$C_6$ alkyl. $R_2$ is selected from hydrogen, hydroxy, and $C_1$-$C_6$ alkoxy, or together $R_1$ and $R_2$ form a single bond. $R_3$, $R_4$, $R^5$, and $R_6$ are the same or different from each other and each represents hydrogen, $C_1$-$C_6$ alkyl, and halogen, or together $R_3$ and $R_4$ with $R_5$ and $R_6$ form an aromatic ring, further wherein the aromatic ring is substituted with one or more X. X is selected from halogen, nitro, amino, and aminocarbonyl. The letter "s" (wherein, the letter s is not enclosed inside a circle e.g. ⓢ) represents 0, 1, 2, or 3, and the letter "t" represents 0, 1, 2, or 3, provided that s+t≧1. $R_7$ and $R_8$ are the same or different from each other and each represents hydroxy, halogen, hydrogen, $C_1$-$C_6$ alkoxy, oxyacyl, or together $R_7$ and $R^8$ form a carbonyl. Y is selected from a methylene or substituted methylene, nucleoside, nucleotide, protected nucleoside, protected nucleotide, $C_5$-$C_8$ aryl, arylalkyl, heteroalkyl, heterocycle, and heteroaryl. In one embodiment, Y is methylene or substituted methylene. The letter "n" determines the number of Y and is selected from 1, 2, 3, 4, 5, 6, 7, 8, 9, and 10.

Z is selected from OR and NHR. R can be hydrogen, $SiR^aR^bR^c$, $CR^aR^bR^c$, heteroalkyl, and $C_1$-$C_6$ alkyl. $R^a$, $R^b$, and $R^c$ are the same as or different from each other and each represents methyl, ethyl, i-propyl, t-butyl, phenyl or substituted phenyl. In some aspects of the invention, R is a protecting group, for example, when R is $SiR^aR^bR^c$ or $CR^aR^bR^c$. As used herein, "protecting group" refers to a grouping of atoms that when attached to a reactive group in a molecule masks, reduces or prevents that reactivity but in a way that allows the original unit to be regenerated at a later point in time. Examples of groups which can be used to protect or mask the reactivity of the oxygen and nitrogen atoms of Z are dimethylethyl, tert-butyl, tert-butyldimethyl silyl (TBDMS), dimethoxytrityl (DMTr), trimethylsilyl (TBS), benzyl, allyl, and the like. In one aspect of the invention, the protecting group is dimethoxytrityl (DMTr or DMT). In another aspect, the protecting group is trimethylsilyl (TBS). Additional examples of protecting groups can be found in Green and Wuts, *Protective Groups in Organic Chemistry*, (Wiley, 2nd ed. 1991); Harrison and Harrison et al., *Compendium of Synthetic Organic Methods*, Vols. 1-8 (John Wiley and Sons, 1971-1996); and Kocienski, *Protecting Groups*, (Verlag, 3rd ed. 2003).

As used herein, the term "methylene" means a —$CH_2$— group. The term "methylene" includes both "unsubstituted methylene" and "substituted methylene" the latter of which refers to methylene moieties having one or both of the hydrogen atoms attached to the carbon atom replaced with a substituent. Such substituents can include for example, alkyl, alkenyl, alkynyl, halogen, hydroxyl, carboxylate, cyano, amino, thio, azide, aryl, heteroaryl, heterocycle, or cycloalkyl.

"Nucleoside" refers to the repeating motif in deoxyribonucleic acid (DNA) and/or ribonucleic acid (RNA). Examples of nucleosides include uridine, cytidine, adenosine, guanosine, deoxythymidine, deoxycytidine, deoxyadenosine, and deoxyguanosine. Nucleoside also includes other naturally occurring and chemically synthesized, modified nucleosides. The term "nucleoside" includes both "unprotected nucleoside" and "protected nucleoside" the latter refers to a nucleoside having one or more protecting groups attached to one or more reactive groups in a nucleoside to mask, reduce, or prevent reactivity. Examples of protecting groups include amides such as benzoyl and substituted benzoyl, isobutryl, acetyl, silyl, trityl and substituted trityl, and cyanoethyl.

"Nucleotide" refers to a phosphorylated nucleoside and includes uridylic acid, cytidylic acid, adenylic acid, guanylic acid, deoxythymidylic acid, deoxycytidylic acid, deoxyadenylic acid, and deoxyguanylic acid. The term "nucleotide" includes both "unprotected nucleotide" and "protected nucleotide" the latter refers to a nucleotide having one or more protecting groups attached to one or more reactive groups in a nucleotide to mask, reduce, or prevent reactivity. Examples of protecting groups include amides such as benzoyl and substituted benzoyl, isobutryl, acetyl, silyl, trityl and substituted trityl, and cyanoethyl.

The linking compound can contain an aromatic ring. In one embodiment, the linking compound refers to a compound of the Formula II:

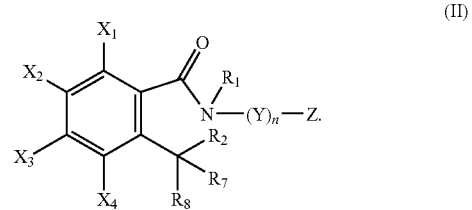

(II)

$R_1$ is selected from hydrogen and $C_1$-$C_6$ alkyl. $R_2$ is selected from hydrogen, hydroxy, oxyacyl, $C_1$-$C_6$ alkoxy, and $C_1$-$C_6$ alkyl, or together $R_1$ and $R_2$ form a single bond. $R_7$ and $R_8$ are each independently selected from hydroxy, halogen, hydrogen, $C_1$-$C_6$ alkoxy, and oxyacyl, or together $R_7$ and $R_8$ form a carbonyl.

The aromatic ring of the linking compound can be substituted. $X_1$, $X_2$, $X_3$, and $X_4$ are selected from hydrogen, halogen, nitro, amino, and aminocarbonyl, wherein at least one of $X_1$, $X_2$, $X_3$, and $X_4$ is not hydrogen. Y is selected from a methylene or substituted methylene, nucleoside, nucleotide, protected nucleoside, protected nucleotide, $C_5$-$C_8$ aryl, arylalkyl, heteroalkyl, heterocycle, and heteroaryl. In one embodiment, Y is methylene or substituted methylene. The letter "n" determines the number of Y and is selected from 1, 2, 3, 4, 5, 6, 7, 8, 9, and 10. Z is selected from OR and NHR. R is selected from hydrogen, $SiR^aR^bR^c$, $CR^aR^bR^c$, heteroalkyl, and $C_1$-$C_6$ alkyl. $R^a$, $R^b$, and $R^cC$ are the same as or different from each other and each represents methyl, ethyl, i-propyl, t-butyl, phenyl or substituted phenyl. In some aspects of the invention, R is a protecting group, for example, when R is $SiR^aR^bR^c$ or $CR^aR^bR^c$. In one aspect of the invention, the protecting group is dimethoxytrityl (DMTr). In another aspect, the protecting group is trimethylsilyl (TBS).

In another aspect, together $R_7$ and $R_8$ form a carbonyl. In another aspect, together $R_1$ and $R_2$ form a single bond. In one aspect, $R_1$ is hydrogen. In another aspect, one of $R_7$ or $R_8$ is $OC(O)CH_3$ and the other is hydrogen. In another aspect, one of $R_7$ or R is hydroxy and the other is hydrogen. $X_2$ is selected from nitro, $-NH_2$, alkylamino, dialkylamino, and aminocarbonyl. In one aspect, $X_2$ is nitro.

In one aspect, Y is a phosphoramidite. As used herein, "phosphoamidite" means a reagent commonly used in synthesis to chemically modify and selectively protect and deprotect nucleosides for example, diisopropylamino-phosphoramidite which is stable until tetrazole is added, cyanoethylphosphoramidite which is stable until ammonia is added, etc. In another aspect, Y is $CH_2$. The letter "n" determines the number of Y and is selected from 1, 2, 3, 4, 5, 6, 7, 8, 9, and 10. In one aspect of the invention, n is 6. In one aspect of the invention, Z is OR. In another aspect, Z is NHR. In one aspect, R is hydrogen. R can also be $Si(t-butyl)(CH_3)_2$ or $C(C_6H_5)(4-MeOC_6H_4)_2$.

In one aspect, at least one of $X_1$, $X_3$, and $X_4$ on the aromatic ring of the compound is halogen. In a further aspect, $X_2$ is nitro or amino. In another aspect, at least one of $X_1$, $X_3$, and $X_4$ is chlorine and $X_2$ is nitro or amino.

In one embodiment, the linking compound is Linking Compound 1, as described by Formula II, wherein $R_1$ and $R_2$ form a single bond. $R_7$ and $R_8$ form a carbonyl (C=O). $X_1$, $X_3$, and $X_4$ are hydrogen. $X_2$ is an amino group. Y is methylene ($CH_2$). The letter "n", which determines the number of Y, is 6. Z is OR, wherein, R is a substituted methyl group. Linking Compound 1 has the following chemical structure:

(Linking Compound 1)

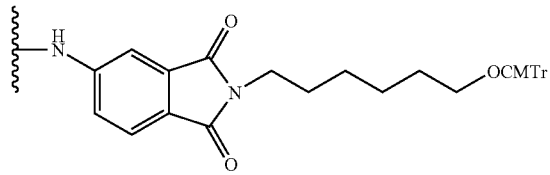

In another embodiment, the linking compound is Linking Compound 2, as described by Formula II, wherein $R_1$ is hydrogen. $R_2$ is an oxyacyl (OAc). $R_7$ and $R_8$ are hydrogen. $X_1$, $X_3$, and $X_4$ are hydrogen. $X_2$ is an amino group. Y is methylene ($CH_2$). The letter "n", which determines the number of Y, is 6. Z is OR., wherein, R is a substituted methyl group. Linking Compound 2 has the following chemical structure:

(Linking Compound 2)

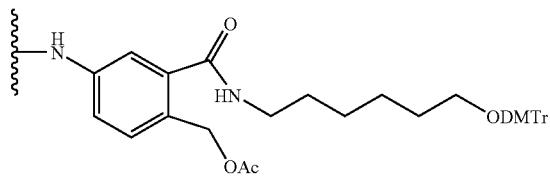

In a third embodiment, the linking compound refers to a compound of the Formula III:

(III)

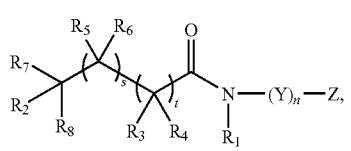

where $R_1$ is selected from hydrogen and $C_1$-$C_6$ alkyl. $R_2$ is selected from hydrogen, hydroxy, $C_1$-$C_6$ alkoxy, and $C_1$-$C_6$ alkyl. $R_3$, $R_4$, $R_5$, and $R_6$ are the same or different from each other and each represents hydrogen, $C_1$-$C_6$ alkyl, or halogen. The letter "s" (wherein, the letter s is not enclosed inside a circle e.g. ⓢ) represents 0, 1, 2, or 3, and the letter "t" represents 0, 1, 2, or 3, provided that $s+t \geq 1$.

$R_7$ and $R^8$ are each independently selected from hydroxy, halogen, hydrogen, $C_1$-$C_6$ alkoxy, oxyacyl, or together $R_7$ and $R^8$ form a carbonyl. Y is selected from a methylene or substituted methylene, nucleoside, nucleotide, protected nucleoside, protected nucleotide, $C_5$-$C_8$ aryl, arylalkyl, heteroalkyl, heterocycle, and heteroaryl. In one embodiment, Y is methylene or substituted methylene. The letter "n" is selected from 1, 2, 3, 4, 5, 6, 7, 8, 9, and 10. Z is selected from OR and NHR. R is selected from hydrogen, $SiR^aR^bR^c$, $CR^aR^bR^c$, heteroalkyl, and $C_1$-$C_6$ alkyl. $R^a$, $R^b$, and $R^c$ are the same or different from each other and each represents methyl, ethyl, i-propyl, t-butyl, phenyl or substituted phenyl. In some aspects of the invention, R is a protecting group, for example, when R is $SiR^aR^bR^c$ or $CR^aR^bR^c$. In one aspect of the invention, the protecting group is dimethoxytrityl (DMTr). In another aspect, the protecting group is trimethylsilyl (TBS). In one aspect, $R_1$ is hydrogen. In another aspect, $R_2$ is hydroxy. In one aspect, together $R_7$ and $R_8$ form a carbonyl.

The linking compound can be substituted. In one aspect, at least one of $R_3$, $R_4$, $R_5$, and $R_6$ is halogen. In another aspect, at least two of $R_3$, $R_4$, $R_5$, and $R_6$ are halogen. In another aspect, at least three of $R_3$, $R_4$, $R_5$, and $R_6$ are halogen. In another aspect, $R_3$, $R_4$, $R_5$, and $R_6$ are each halogen. In one aspect, halogen is fluorine. In another aspect of the invention, Z is hydroxy. In another aspect of the invention, Z is $OSi(t-butyl)(CH_3)_2$. In another aspect of the invention, Z is $OC(C_6H_5)(4-MeOC_6H_4)_2$. In one aspect of the invention, Y is $CH_2$. In another aspect, n is 6.

Another embodiment of the present invention provides a compound that can be used as a solid support reagent for synthesis as shown in Formula IV (IV)

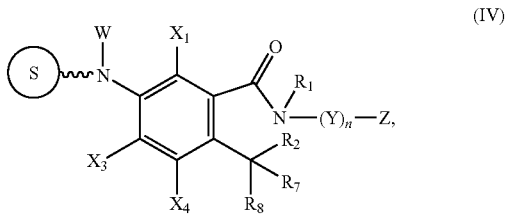

where ⓢ is a solid support. The symbol "⋯" or "the wavy line" represents a carbon linker which optionally contains a carbonyl. In one embodiment, the carbonyl is adjacent to the nitrogen atom substituted with W e.g.

(IVA)

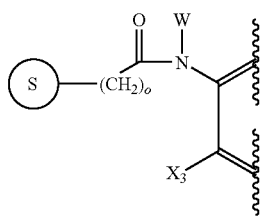

or

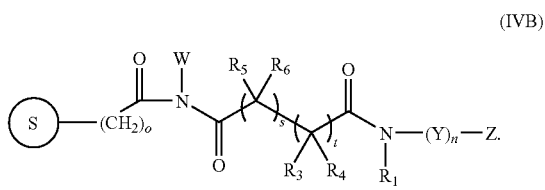

The letter "o" represents the number of methylene groups. The letter o is selected from 0-20 atoms. In one embodiment, the letter o is selected from 0, 1, 2, 3, 4, 5, 6, 7, 8, 9, 10. In one embodiment, o is 0. In another embodiment, the letter o is 6. In one embodiment, the carbon chain can be substituted. In one embodiment, the carbon chain is an alkyl chain. In one embodiment, the carbon chain is an alkyl chain which contains a carbonyl. Alkyl chain linkers are known in the art as short molecules which serve to connect solid support functional groups (e.g., hydroxyl groups) or compounds which display functional groups (e.g. linking compounds). Suitable linkers are disclosed in, for example, Oligonucleotides And Analogues A Practical Approach, Ekstein, F. Ed., IRL Press, N.Y., 1991, Chapter 1.

The nitrogen atom directly attached to the aromatic ring of the linking compound can be unsubstituted (W=H) or substituted with an alkyl group. For example, W is hydrogen or $C_1$-$C_6$ alkyl.

In the compounds of Formula IV,

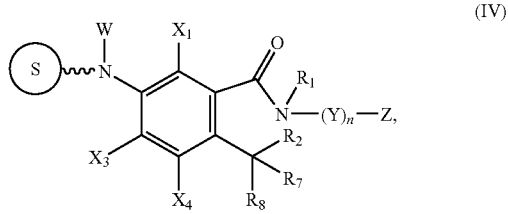

$R_1$ is selected from hydrogen and $C_1$-$C_6$ alkyl. $R_2$ is selected from hydrogen, hydroxy, oxyacyl, $C_1$-$C_6$ alkoxy, and $C_1$-$C_6$ alkyl, or together $R_1$ and $R_2$ form a single bond. $R_7$ and $R_8$ are each independently selected from hydroxy, halogen, hydrogen, $C_1$-$C_6$ alkoxy, oxyacyl, or together $R_7$ and $R_8$ form a carbonyl. The aromatic ring of the linking compound in Formula IV can be substituted. For example, $X_1$, $X_3$, and $X_4$ are selected from hydrogen, halogen, nitro, amino and aminocarbonyl. Y is selected from a methylene or substituted methylene, nucleoside, nucleotide, protected nucleoside, protected nucleotide, $C_5$-$C_8$ aryl, arylalkyl, heteroalkyl, heterocycle, and heteroaryl. The letter "n" is determines the number of Y and is selected from 1, 2, 3, 4, 5, 6, 7, 8, 9, and 10. Z is selected from OR and NHR. R is selected from hydrogen, $SiR^aR^bR^c$, $CR^aR^bR^c$, heteroalkyl, and $C_1$-$C_6$ alkyl. $R^a$, $R^b$, and $R^c$ are the same as or different from each other and each represents methyl, ethyl, i-propyl, t-butyl, phenyl or substituted phenyl. In one aspect of the invention, R is a protecting group, for example, when R is $SiR^aR^bR^c$ or $CR^aR^bR^c$. In one aspect of the invention, the protecting group is dimethoxytrityl (DMTr). In another aspect, the protecting group is trimethylsilyl (TBS).

In another aspect of the invention, the solid support of Formula IV is selected from controlled pore glass (CPG), styrene-divinylbenzene (DVB) co-polymer, polyethylene glycol (PEG), and a methacrylate based polymer. The wavy line in Formula IV represents a carbon chain which optionally contains one or more carbonyl groups. The carbon chain forms a linker between the solid support and the linking compound. The carbonyl group or groups can be located at any position of the carbon chain. In one aspect, the carbonyl group in the carbon chain is adjacent to the nitrogen atom attached to the aromatic ring e.g.,

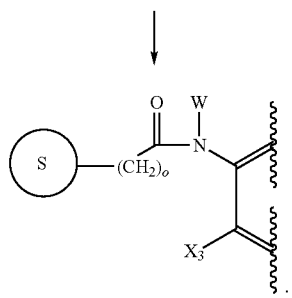

In another aspect, o is 0 i.e., the wavy line is a carbonyl.

In one embodiment of the present invention, the solid support reagent for synthesis, as defined by Formula IV, describes Solid Support Reagent 1 (16) wherein the wavy line ∿∿∿ between the solid support and the lining compound is a carbonyl, $R_1$ and $R_2$ form a single bond. $R_7$ and $R_8$ form a carbonyl. $X_1$, $X_3$, and $X_4$ are hydrogen. W is a hydrogen. Y is methylene ($CH_2$). The letter "n", which determines the number of Y, is 6. Z is OR, wherein, R is a dimethoxytrityl group. While it is not intended that the present invention be limited to any specific solid supports, examples of solid support which may be used in Solid Support Reagent 1 (16) include controlled pore glass (CPG), styrene-divinylbenzene (DVB) co-polymer, polyethylene glycol (PEG), and a methacrylate based polymer.

Solid Support Reagent 1 (16) has the following chemical structure:

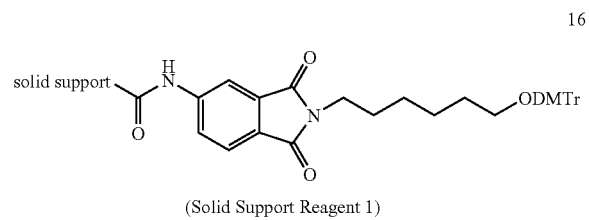

(Solid Support Reagent 1)

In another embodiment of the present invention, the solid support reagent for synthesis, as defined by Formula IV, describes Solid Support Reagent 2 (22), wherein, the wavy line ∿∿∿ between the solid support to the linking compound is a carbonyl, $R_1$ is hydrogen. $R_2$ is an oxyacyl (OAc). $R_7$ and $R_8$ are hydrogen. $X_1$, $X_3$, and $X_4$ are hydrogen. W is a hydrogen. Y is methylene ($CH_2$). The letter "n", which determines the number of Y, is 6. Z is OR, wherein, R is a dimethoxytrityl group. While it is not intended that the present invention be limited to any specific solid supports, examples of solid supports which may be used in Solid Support Reagent 2 (22) include controlled pore glass (CPG), styrene-divinylbenzene (DVB) co-polymer, polyethylene glycol (PEG), and a methacrylate based polymer.

Solid Support Reagent 2 (22) has the following chemical structure:

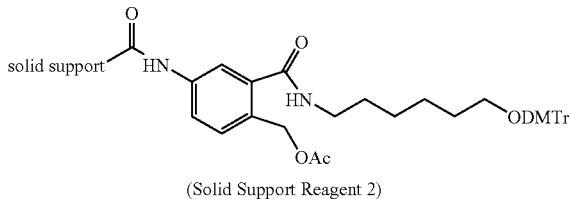

(Solid Support Reagent 2)

Another embodiment of the present invention provides a compound that can be used as a solid support reagent for synthesis as shown in Formula V

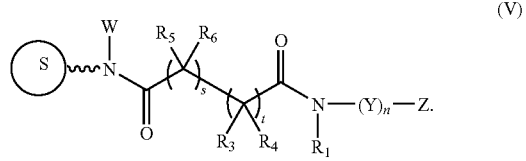

(V)

The symbol "Ⓢ" represents a solid support. The wavy line ⁓ represents a carbon chain which optionally contains a carbonyl. W is selected from hydrogen and $C_1$-$C_6$ alkyl. $R_1$ is selected from hydrogen and $C_1$-$C_6$ alkyl. $R_3$, $R_4$, $R_5$, and $R_6$ are the same or different from each other and each represents hydrogen, $C_1$-$C_6$ alkyl, or halogen. The letter "s" (wherein, the letter s is not enclosed inside a circle e.g. ⓢ) represents 0, 1, 2, or 3. The letter "t" represents 0, 1, 2, or 3, provided that s+t≦1. Y is selected from a methylene or substituted methylene, nucleoside, nucleotide, protected nucleoside, protected nucleotide, $C_5$-$C_8$ aryl, arylalkyl, heteroalkyl, heterocycle, and heteroaryl. In one embodiment, Y is methylene or substituted methylene. The letter "n" determines the number of Y and is selected from 1, 2, 3, 4, 5, 6, 7, 8, 9, and 10. Z is selected from OR and NHR. R is selected from hydrogen, $SiR^aR^bR^c$, $CR^aR^bR^c$, heteroalkyl, and $C_1$-$C_6$ alkyl. $R^a$, $R^b$, and $R^c$ are the same or different from each other and each represents methyl, ethyl, i-propyl, t-butyl, phenyl or substituted phenyl. In one aspect of the invention, R is a protecting group, for example, when R is $SiR^aR^bR^c$ or $CR^aR^bR^c$. In one aspect of the invention, the protecting group is dimethyoxytrityl (DMTr). In another aspect of the invention, the protecting group is trimethylsilyl (TBS). In another aspect, the solid support is selected from controlled pore glass (CPG), styrene-divinylbenzene (DVB) co-polymer, polyethylene glycol (PEG), or methacrylate based polymers. The wavy line which represents an carbon chain optionally contains one or more carbonyl groups. The carbonyl groups can be located anywhere along the carbon chain. In one embodiment, the carbon chain is an alkyl chain containing a carbonyl. In another embodiment, o is 0. In one aspect, the carbonyl in the alkyl chain is adjacent to the nitrogen atom substituted with W—in the linking compound e.g.,

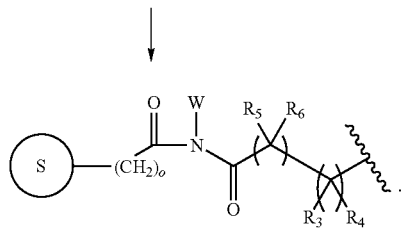

Detailed descriptions of the chemistry used to form oligonucleotides are provided elsewhere e.g., Agrawal, S. ed. Protocols for Oligonucleotides and Analogs, Humana Press, Totowa, N.J., 1993, ISBN 0-89603-247-7. In one embodiment, the oligonucleotides are synthesized using the phosphoramidite method. Advantages of using the phosphoramidite method include increased yields and stability and availability of starting materials. The synthesis is performed with the oligonucleotide chain attached to a solid support, so that excess reagents, which are in the liquid phase, can be easily removed by filtration, thereby eliminating the need for purification steps between cycles. The synthetic process of the present invention can be conducted manually. Alternatively, the synthetic process can be automated.

The following is an example of using the method of the present invention to synthesize a compound having a defined composition involving the following steps (see FIG. 1). First, a solid support reagent is selected (step a). The solid support reagent is prepared by attaching the linking compounds of Formula I, II or III to a solid support. Formula IV, IVA, IVB, or V, as described above, are examples of suitable solid support reagents. Throughout FIG. 1, the solid support reagent is referred to as "A". The functional groups of A which involved in the coupling reaction are shown as attached to A e.g. —OR or —O⁻.

Second, the first O—R or N—R bond is cleaved to form a first deprotected oxygen or first deprotected nitrogen (step b). A "deprotected oxygen" or "deprotected nitrogen" means a hydroxyl group (—OH or —O⁻) or amino group (—NH₂ or —NH⁻), with its R group removed which makes it available for reaction in a subsequent coupling reaction. The O—R or N—R bond can be cleaved using a variety of conditions, for example, treatment of the solid support with an acid such as trichloroacetic or dichloroacetic acid or Lewis acids such as $BF_3$ or $ZnBr_2$.

Next, the first deprotected oxygen or first deprotected nitrogen is reacted with a first molecule containing a second OR or second NHR, thereby attaching the first molecule to the first deprotected oxygen or first deprotected nitrogen. The "molecule" can be any chemical moiety including, but not limited to, a nucleotide, amino acid, or saccharide. The molecule may or may not be protected with a protecting group. In one embodiment, the first and second molecules are protected nucleotides. In another embodiment, the nucleotides are 5'-protected nucleotides.

In one embodiment, the 3'-termini of each nucleotide that is reacted in sequential steps of the reaction is attached to a first or second deprotected oxygen or deprotected nitrogen. In another embodiment, the first and second molecules are protected amino acids. In another embodiment, the first and second molecules are protected saccharides. The molecule may include an activated intermediate, which is formed when the protected molecule and an activating reagent are simultaneously added to the reaction mixture. For example, the activating reagent can be a weak acid such a tetrazole which protonates the nitrogen of a phosphoramidite thus forming a reactive intermediate.

Optionally, a capping step may be performed after step c or step e to terminate any oligomer chains that did not undergo attachment of the first or second molecule. In one embodiment, the capping step involves a base such as N-methylimidazole and a carboxcylic anhydride such as acetic anhydride or isobutric anhydride. The purpose of a capping step is to stop further reaction of any hydroxyl or amino group that did not react e.g., with the phosphoramidite building block.

The second O—R or N—R bond is then cleaved to form a second deprotected oxygen or second deprotected nitrogen to form a hydroxyl group (—OH or —O⁻) or amino group (—NH₂ or —NH⁻) (step d), with its R group removed and which is available for reaction in a subsequent reaction. The O—R or N—R bond is cleaved using a variety of conditions as discussed above. Next, a second molecule containing a third OR or third NHR is reacted with the second deprotected oxygen or second deprotected nitrogen from step d, thereby attaching the second molecule to the second deprotected oxygen or second deprotected nitrogen. As described above, a capping step may be performed to terminate any oligomer chains that did not undergo addition of the first or second molecule. Steps d and e are repeated until a compound of a desired composition is obtained (step f).

After synthesis, the compound having a defined composition can be disconnected from the solid support using a variety of reagents. A "compound having a defined composition" or "compound of a desired composition" means a compound which is made up of the molecules employed in the series of reactions carried out, for example a compound of a defined composition can be an oligomeric compound of desired length. In one aspect, a compound of a desired composition is an oligonucleotide with the desired number of nucleotides attached together to form the compound. In another aspect, a compound of a desired composition is a peptide with the desired number of amino acids attached together to form the compound. In another aspect, a compound of a desired composition is an oligosaccharide with the desired number of saccharides attached together to form the compound. In another embodiment, a compound of a desired composition is a small molecule with the desired number of molecules attached together to form the compound. Reaction conditions to disconnect the compound from the solid support can be acidic, basic, or neutral. In one embodiment, typical reaction conditions involve incubating the support with a strong base such as ammonia hydroxide or methylamine in water or alcohol for several minutes to several hours from room temperature to 65° C. In some embodiments, the cleavage reagent may also remove any other protecting groups on the oligonucleotide.

In one embodiment, the compound removed from the solid support is isolated. The compound can be isolated using a variety of techniques or methods e.g., high performance liquid chromatography (HPLC), recrystallization, etc. "To isolate a compound" means to subject the compound a procedure or method in order to free the compound from other substances such as other compounds for example, oligomers of incomplete reaction i.e. the oligomer has a molecule missing, isomers, impurities, etc. A compound can be subjected to an isolation procedure one or more times. Isolation of the compound may result in a compound that contains fewer impurities than the original compound disconnected from the solid support, i.e. the compound has been purified. For example, the compound of desired composition is an oligonucleotide. In another embodiment, the oligonucleotide is a mixed base sequence. "Mixed base sequence" means that the oligonucleotide contains different bases e.g., A-T-G-C-C-T-G (SEQ ID NO: 1). In another embodiment, the oligonucleotide contains the same bases, e.g., a homopolymer such as A-A-A-A (SEQ ID NO: 2).

In one embodiment, the compound is a peptide. In another embodiment, the compound is an oligosaccharide. In another embodiment, the compound is a small molecule.

The present invention is not limited to any specific solid support. In selected embodiments of the present invention, the solid support is selected from controlled pore glass (CPG), styrene-divinylbenzene (DVB) co-polymer, polyethylene glycol (PEG) or methacrylate based polymers.

A variety of methods can be used to disconnect the compound from the solid support. In one embodiment, the compound can be disconnected as shown below by cleaving the following bonds:

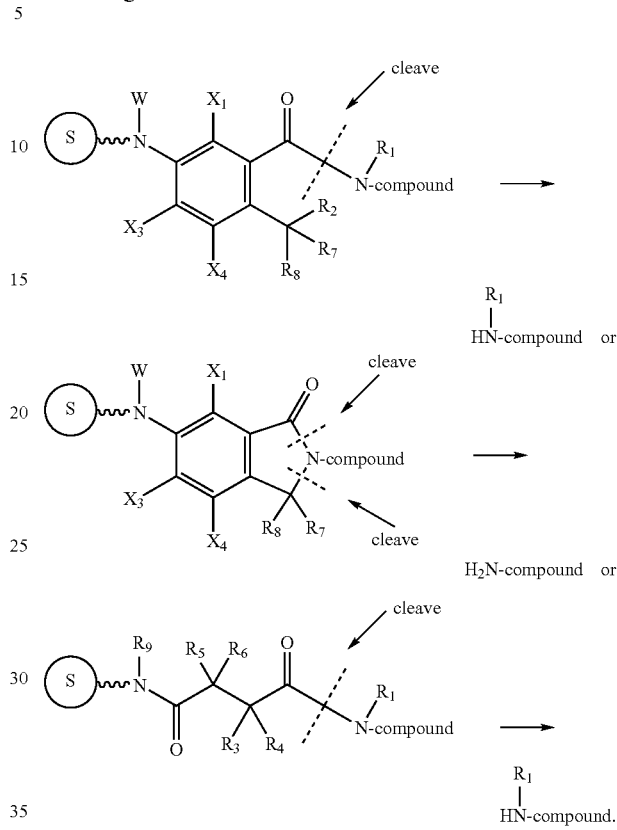

Conditions which can be used to cleave the bonds as shown above include 40% aqueous methylamine for 2 hours at 45° C.

In one embodiment, the invention includes a derivatized compound having a nucleotide with a 3' terminus attached to a compound of Formula IVa:

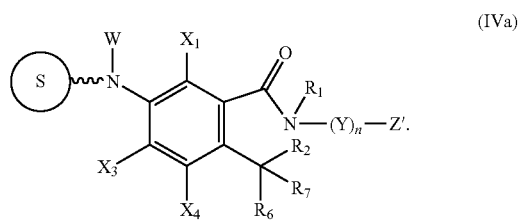

The symbol "Ⓢ" represents a solid support. The wavy line ∿∿∿ represents a carbon chain which optionally contains a carbonyl. W is selected from hydrogen and $C_1$-$C_6$ alkyl. $R_1$ is selected from hydrogen and $C_1$-$C_6$ alkyl. $R_2$ is selected from hydrogen, hydroxy, oxyacyl, $C_1$-$C_6$ alkoxy, and $C_1$-$C_6$ alkyl, or together $R_1$ and $R_2$ form a single bond. $R_7$ and $R_8$ are each independently selected from hydroxy, halogen, hydrogen, $C_1$-$C_6$ alkoxy, oxyacyl, or together $R_7$ and $R_8$ form a carbonyl. $X_1$, $X_3$, and $X_4$ are selected from hydrogen, halogen, nitro, amino, and aminocarbonyl. Y is selected from a methylene or substituted methylene, nucleoside, nucleotide, protected nucleoside, protected nucleotide, $C_5$-$C_8$ aryl, arylalkyl, heteroalkyl, heterocycle, and heteroaryl. In one embodiment, Y is methylene or substituted methylene. The letter "n" determines the number of Y and is 1, 2, 3, 4, 5, 6, 7, 8, 9, or 10. Z' is selected from OR and NHR. R is selected from nucleotide or oligonucleotide. $R^a$, $R^b$, and $R^c$ are the same as or different from each other and each represents methyl, ethyl, i-propyl, t-butyl, phenyl or substituted phenyl.

In one embodiment, the solid support of the derivatized compound of Formula IVa is selected from controlled pore glass (CPG) or styrene-divinylbenzene (DVB) co-polymer, polyethylene glycol (PEG) or methacrylate based polymers. In another embodiment, the carbonyl in the carbon chain represented by a wavy line of the derivatized compound of Formula IVa is adjacent to the nitrogen atom on the aromatic ring.

In another embodiment, the invention includes a derivatized compound having a nucleotide with a 3' terminus attached to a solid support reagent of Formula Va:

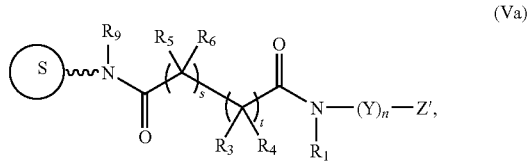

(Va)

where Ⓢ is a solid support. The symbol "⌇⌇⌇" or wavy line represents a carbon chain which optionally contains a carbonyl. W is selected from hydrogen and $C_1$-$C_6$ alkyl. $R_1$ is selected from hydrogen and $C_1$-$C_6$ alkyl. $R_3$, $R_4$, $R_5$, and $R_6$ are the same or different from each other and each represents hydrogen, $C_1$-$C_6$ alkyl, or halogen. The letter "s" (where the letter s is not enclosed inside a circle) represents 0, 1, 2, or 3. The letter "t" represents 0, 1, 2, or 3, provided that s+t≦1. Y is selected from a methylene or substituted methylene, nucleoside, nucleotide, protected nucleoside, protected nucleotide, $C_5$-$C_8$ aryl, arylalkyl, heteroalkyl, heterocycle, and heteroaryl. In one embodiment, Y is methylene or substituted methylene. The letter "n" determines the number of Y and is selected from 1, 2, 3, 4, 5, 6, 7, 8, 9, or 10. Z' is selected from OR and NHR. R is selected from nucleotide or oligonucleotide. $R^a$, $R^b$, and $R^c$ are the same or different from each other and each represents methyl, ethyl, i-propyl, t-butyl, phenyl or substituted phenyl.

In one embodiment, the solid support of the derivatized compound of Formula Va is selected from controlled pore glass (CPG) or styrene-divinylbenzene (DVB) co-polymer, polyethylene glycol (PEG) or methacrylate based polymers. In another embodiment, the carbonyl in the carbon chain of the derivatized compound of Formula Va is adjacent to the nitrogen atom on the aromatic ring.

The above description sets forth rather broadly the more important features of the present invention in order that the detailed description thereof that follows may be understood, and in order that the present contributions to the art may be better appreciated. Other objects and features of the present invention will become apparent for the following detailed description considered in conjunction with any examples.

Definitions

For convenience, certain terms used in the specification, examples and appended claims are collected here.

The terms "oligonucleotide" or "polynucleotide" as used herein refer to oligomers of natural or modified nucleoside or of non-nucleoside analogs linked by phophodiester bonds or analogs thereof ranging in size from a few monomeric units, e.g., 2-5, to several hundred monomeric units.

"Alkyl" includes saturated aliphatic groups, including straight-chain alkyl groups (e.g., methyl, ethyl, propyl, butyl, pentyl, hexyl, heptyl, octyl, nonyl, decyl), branched-chain alkyl groups (e.g., isopropyl, tert-butyl, isobutyl), cycloalkyl (e.g. alicyclic) groups (e.g., cyclopropyl, cyclopentyl, cyclohexyl, cycloheptyl, cyclooctyl), alkyl substituted cycloalkyl groups, cycloalkyl substituted alkyl groups, and heteroalkyl groups. Alkyl groups having heteroatoms in the alkyl group may also be referred to as "heteroalkyls". Examples of heteroalkyl groups include —$CH_2OCH_3$, $CH_2OR^d$, where $R^d$ is alkyl or substituted alkyl e.g. $C(CH_3)_3$, or $CHR^eR^d$, where $R^e$ is an alkyl group. In certain embodiments, a straight chain or branched chain alkyl has six or fewer carbon atoms in its backbone (e.g., $C_1$-$C_6$ for straight chain, $C_3$-$C_6$ for branched chain), and in other embodiments four or fewer carbon atoms. Likewise, cycloalkyls have from three to eight carbon atoms in their ring structure, and in other embodiments have five or six carbons in the ring structure. "$C_1$-$C_6$" includes alkyl groups containing 1, 2, 3, 4, 5, or 6 carbon atoms. Unless the number of carbons is otherwise specified, "lower alkyl" includes an alkyl group, as defined above, but having 1, 2, 3, 4, 5, 6, 7, 8, 9, or 10 carbon atoms, in another embodiment, an alkyl group has 1, 2, 3, 4, 5, or 6 carbon atoms in its backbone structure.

"Aryl" or "aromatic ring" includes groups with aromaticity, including 5- and 6-membered "unconjugated", or single-ring, aromatic groups that may include 0, 1, 2, 3, or 4 heteroatoms, as well as "conjugated" or multicyclic systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. "$C_5$-$C_8$" includes aryl groups containing 5, 6, 7, or 8 carbon atoms.

Those aryl groups having heteroatoms in the ring structure may also be referred to as "aryl heterocycles", "heterocycles," "heteroaryls" or "heteroaromatics". The aromatic ring can be substituted at one or more ring positions with substituents such as for example, alkyl, halogen, hydroxyl, alkoxy, alkylcarbonyloxy, arylcarbonyloxy, alkoxycarbonyloxy, carboxylate, alkylcarbonyl, alkylaminocarbonyl, alkylcarbonyl, alkoxycarbonyl, aminocarbonyl, alkylthiocarbonyl, phosphate, phosphonato, phosphinato, cyano, amino (including —$NH_2$, alkylamino, dialkylamino, arylamino, diarylamino, and alkylarylamino), acylamino (including alkylcarbonylamino, arylcarbonylamino, carbamoyl, and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, and azido.

"Acyl" includes compounds and moieties that contain the acyl radical ($CH_3CO$—) or a carbonyl group. "Substituted acyl" includes acyl groups where one or more of the hydrogen atoms are replaced by for example, alkyl groups, halogens, hydroxyl, alkoxyl, amino (including —$NH_2$, alkylamino, dialkylamino, arylamino), alkylthio, arylthio, nitro, trifluoromethyl, cyano, and azido moiety. The term "oxyacyl" means —$OC(O)CH_3$.

"Amino" includes compounds and moieties that contain $NH_2$, alkylamino, dialkylamino, arylamino, diarylamino, and alkylarylamino. One example of an amino group is:

amino group

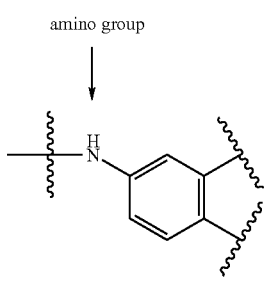

The term "alkoxy" or "alkoxyl" includes substituted and unsubstituted alkyl groups covalently linked to an oxygen atom. Examples of alkoxy groups (or alkoxyl radicals) include methoxy, ethoxy, isopropyloxy, propoxy, butoxy, and pentoxy groups. Examples of substituted alkoxy groups include halogenated alkoxy groups. Examples of halogen substituted alkoxy groups include, but are not limited to, fluoromethoxy, difluoromethoxy, trifluoromethoxy, chloromethoxy, dichloromethoxy, and trichloromethoxy.

The term "carbon chain" refers to alkyl, alkenyl, and alkynyl chains. The term "carbon chain which optionally contains a carbonyl" refers to a carbonyl chain e.g., —C(O)— or a carbon chain containing a carbonyl e.g., an alkyl chain containing a carbonyl —$CH_2CH_2C(O)$— or —$CH_2C(O)CH_2$—.

The terms "heterocyclyl", "heterocycle" or "heterocyclic" group include closed ring structures, e.g., 3, 4, 5, 6, 7, 8, 9, or 10-, or 4, 5, 6, or 7-membered rings, which include one or more heteroatoms. In one embodiment, the ring structure is a 5 or 6-membered ring. "Heteroatom" includes atoms of any element other than carbon or hydrogen. Examples of heteroatoms include nitrogen, oxygen, sulfur and phosphorus.

Heterocyclyl groups can be saturated or unsaturated and include for example, pyrrolidine, oxolane, thiolane, piperidine, piperazine, morpholine, lactones, lactams such as azetidinones and pyrrolidinones, sultams, and sultones. Heterocyclic groups e.g., pyrrole and furan can have aromatic character. Heterocyclic groups include fused ring structures such as quinoline and isoquinoline. Other examples of heterocyclic groups include pyridine and purine. The heterocyclic ring can be substituted at one or more positions.

The term "hydroxy" or "hydroxyl" includes groups with an —OH or —$O^-$.

The term "halogen" includes fluorine, bromine, chlorine, iodine, etc. The term "perhalogenated" generally refers to a moiety wherein all hydrogens are replaced by halogen atoms.

It will be noted that the structure of some of the compounds of the invention include asymmetric (chiral) carbon atoms. It is to be understood accordingly that the isomers arising from such asymmetry are included within the scope of the invention, unless indicated otherwise. Such isomers can be obtained in substantially pure form by classical separation techniques and by stereochemically controlled synthesis. The compounds of this invention may exist in stereoisomeric form, therefore can be produced as individual stereoisomers or as mixtures.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al, *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J., Chem. Educ.* 1964, 41, 116).

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure and are substituted with various groups as described herein. For example, all of the compounds represented by Formula I are derivatives and have Formula I as a common core.

"Small molecule" means a compound with a molecular weight of less than 800 atomic mass units.

The invention will be further clarified by a consideration of the following examples, which are intended to be purely exemplary of the invention and not to in any way limit its scope.

EXAMPLES

Schemes 1-5, shown below, depict the synthesis of several linking compounds and solid phase reagents that are embodiments of the present invention.

Example 1

Scheme 1 below shows the preparation of compounds of the Formula IV, where $R_1$ and $R_2$ form a single bond and together $R_7$ and $R_8$ form a carbonyl. The synthesis begins with the reaction of benzofuran 1 with the primary amine 3, where Y can be selected from a methylene or substituted methylene, nucleoside, nucleotide, protected nucleoside, protected nucleotide, $C_5$-$C_8$ aryl, arylalkyl, heteroalkyl, heterocycle, and heteroaryl, and n can be 1-10. The aromatic ring of the benzofuran moiety can be optionally substituted, for example with halogen atoms such as F or Cl. The hydroxyl group can be protected to form compound 2, where R can be selected from hydrogen, $SiR^aR^bR^c$, $CR^aR^bR^c$, heteroalkyl, and $C_1$-$C_6$ alkyl, and $R^a$, $R^b$, and $R^c$ can be the same as or different from each other and each can represent methyl, ethyl, i-propyl, t-butyl, phenyl or substituted phenyl. The aromatic nitro group of 2 can be reduced for example, using hydrogen to form a primary amine which can then be coupled to a commercially available solid support derivatized with an acid functionality to form the solid support reagent 3.

Scheme 1

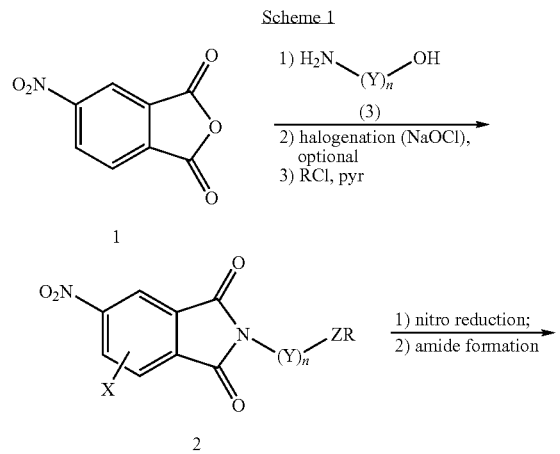

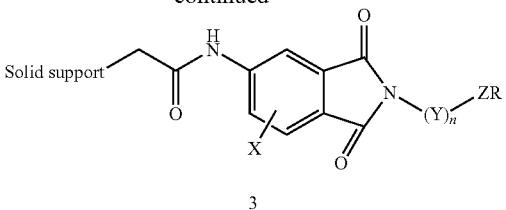

X = H, Cl;
Y = $CH_2$, nucleoside, aromatic
R = DMT, TBS, etc;
n = 1, 2, 3, 4, 5, 6...;
Z = O, N

Example 2

Scheme 2 below shows the preparation of compounds of the Formula IV, where one of $R_2$, $R_7$, and $R_8$ is oxyacyl and the remaining $R_2$, $R_7$, and $R_8$ are hydrogen. The synthesis begins with the reaction of benzofuranone 4 with amine 3 to form an amide, where Y can be selected from a methylene or substituted methylene, nucleoside, nucleotide, protected nucleoside, protected nucleotide, $C_5$-$C_8$ aryl, arylalkyl, heteroalkyl, heterocycle, and heteroaryl, and n can be 1-10. The hydroxyl group attached to Y can be protected to form compound 5, where Z is OR and R can selected from hydrogen, $SiR^aR^bR^c$, $CR^aR^bR^c$, heteroalkyl, and $C_1$-$C_6$ alkyl, and $R^a$, $R^b$, and $R^c$ can be the same as or different from each other and each can represent methyl, ethyl, i-propyl, t-butyl, phenyl or substituted phenyl. The remaining hydroxyl group in 5 can be protected as an acetate using acetic anhydride, pyridine, and DMAP catalyst to form compound 6. The aromatic nitro group of 6 can be reduced to form an amine for example, using hydrogen with nickel catalyst. The primary amine can then be coupled to a commercially available solid support derivatized with a carboxylic acid to form the solid support reagent 7.

Scheme 2

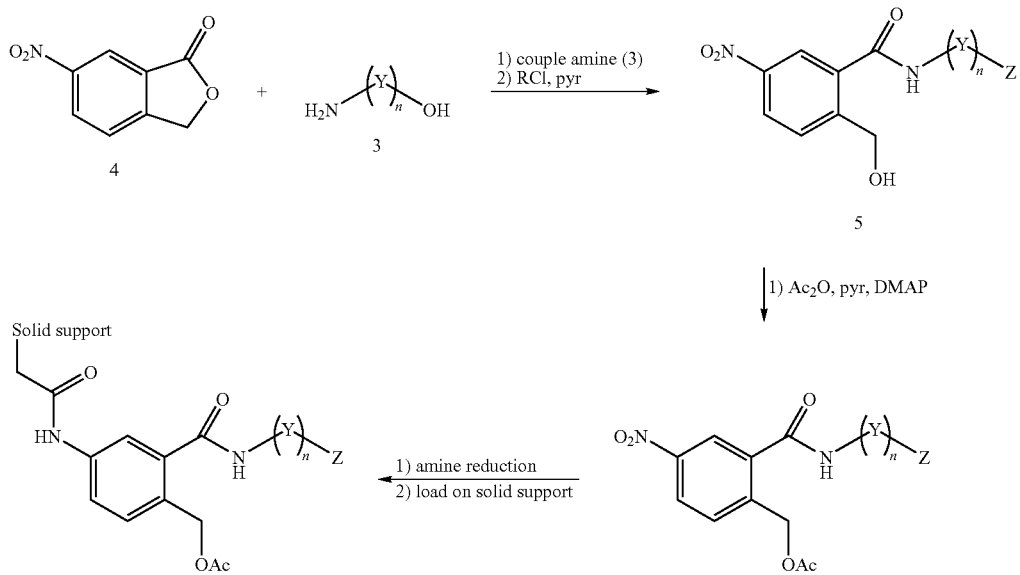

n = 1, 2, 34, 5, 6...;
Z = O, N;
Y = $CH_2$, nucleoside, aromatic;
R = DMT, TBS, etc

Example 3

Scheme 3 below shows the preparation of compounds of the Formula V, where for example, $R_3$ and $R_4$ are both F, $t=1-3$ and $s=0$ or $R_5$ and $R_6$ are both F, $s=1-3$ and $t=0$. The synthesis begins with the coupling of dihydrofurandione 8 with amine 3 to form the amide 9. The primary hydroxyl group of 9 can be protected using a chloride reagent R—Cl and pyridine to form 10, where Y can be selected from a methylene or substituted methylene, nucleoside, nucleotide, protected nucleoside, protected nucleotide, $C_5$-$C_8$ aryl, arylalkyl, heteroalkyl, heterocycle, and heteroaryl, and n can be 1-10. R can be selected from hydrogen, $SiR^aR^bR^c$, $CR^aR^bR^c$, heteroalkyl, and $C_1$-$C_6$ alkyl, and $R^a$, $R^b$, and $R^c$ can be the same as or different from each other and each can represent methyl, ethyl, i-propyl, t-butyl, phenyl or substituted phenyl. The carboxylic acid of 10 can then be coupled to a commercially available solid support derivatized with an amide moiety to form the solid support reagent 11.

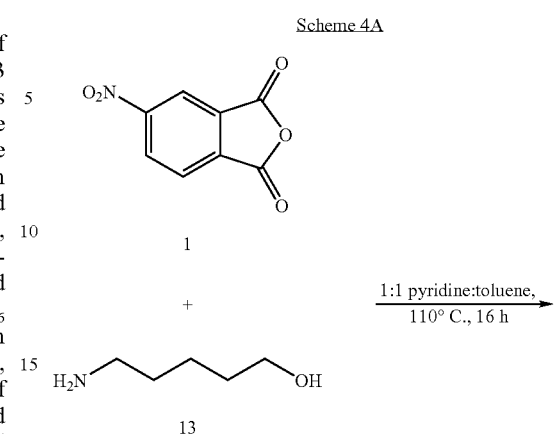

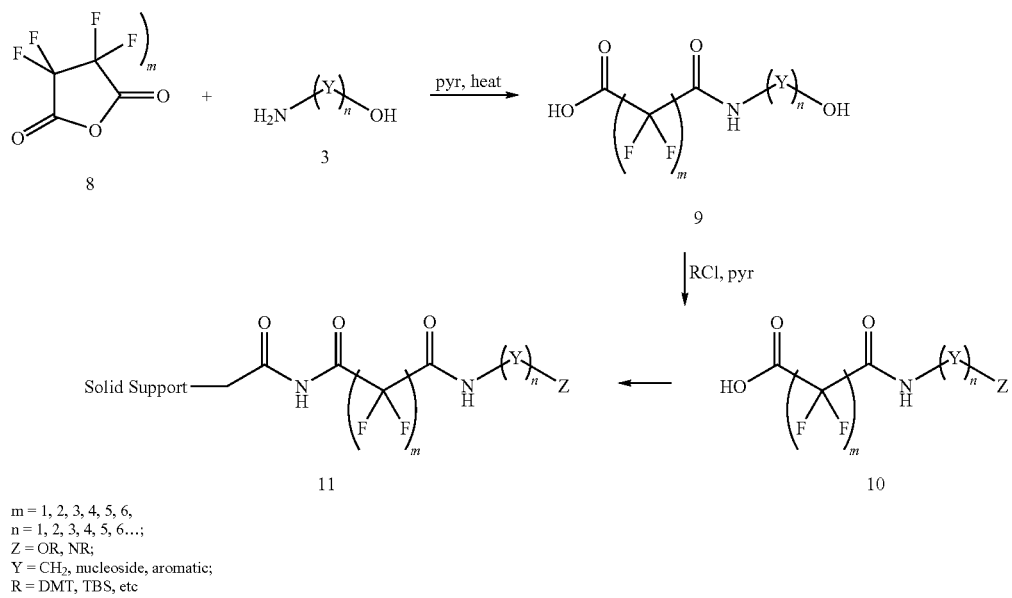

m = 1, 2, 3, 4, 5, 6,
n = 1, 2, 3, 4, 5, 6...;
Z = OR, NR;
Y = $CH_2$, nucleoside, aromatic;
R = DMT, TBS, etc

Example 4

Schemes 4A-4C shown below describe the synthesis of Linking Compound 1 and Solid Support Reagent 1 (16).

Scheme 4

Step 1:

4-Nitrophthalimide 1 (Aldrich 253979) (10 g, 0.052 mol) and 6-amino-1-hexanol 13 (TCI A1027) (6.7 g, 0.057 mol) were suspended in 150 mL of pyridine and 150 mL of toluene in a 3-neck round bottom flask equipped with a stir bar, reflux condenser, and temperature probe. The heterogeneous solution was heated to reflux (110° C.). The solution became homogeneous during the temperature increase to 110° C. After a total of 16 hours at 110° C., the heating was discontinued and the reaction is allowed to cool to room temperature. Concentration of the heterogeneous solution under reduced pressure yielded a solid off-white product 14. The yield of this product 14 was greater than 90%.

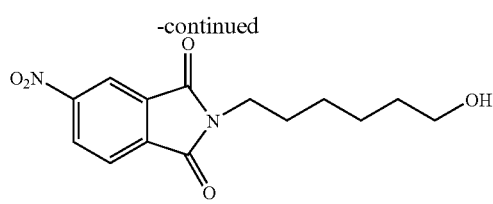

Step 2:

As shown in Scheme 4B, the product 14 from Step One (azeotroped 3×75 mL with pyridine) was dissolved in 200 mL of pyridine. Dimethoxytrityl chloride (ChemGenes RN-1401) (15.8 g, 0.0468 mol) was added in 4 portions over 1 hour. The reaction was stirred under argon overnight. The reaction was quenched with 5 mL of methanol and concentrated to a paste. The paste was then dissolved in dichloromethane (DCM) (200 mL) and the organic layer washed with water (1×100 mL), cold 10% citric acid (2×100 mL), and brine (1×100 mL). The organic layer was dried over MgSO₄, and filtered. The crude material was purified in DCM:methanol on silica gel and evaporated to yield the protected nitro alcohol. The nitro group was reduced by hydrogenation on palladium on carbon in methanol to yield the product 15 in 70% overall yield.

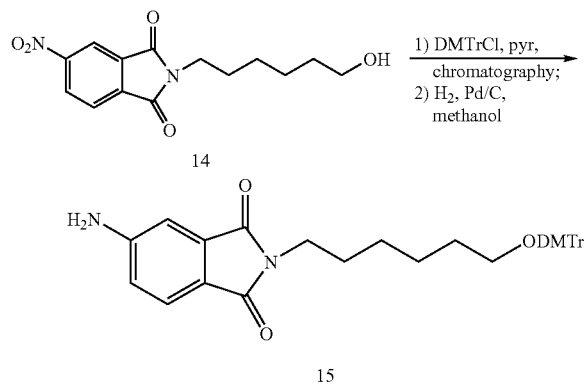

As shown below in Scheme 4C, the primary amine of the product 15 was then coupled to a commercially available solid support derivatized with a carboxylic acid to form the solid support reagent 16 (Solid Support Reagent 1).

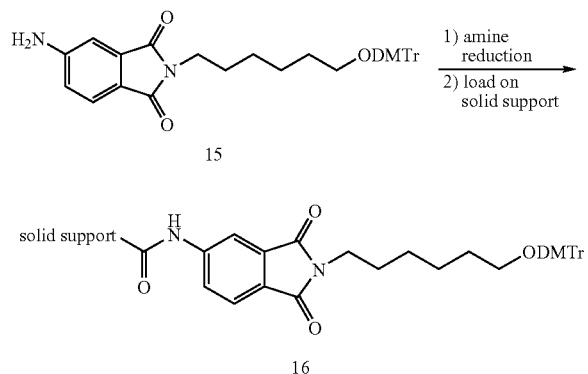

Example 5

Schemes 5 A-D shown below describe the synthesis of Linking Compound 2 and Solid Support Reagent 2.

Scheme 5

Step 1:

As shown below in Scheme 5A, 6-Nitrophthalide 4 (Aldrich 115932) (10 g, 0.052 mol) and 6-amino-1-hexanol 13 (TCI A1027) (6.7 g, 0.057 mol) was suspended in 150 mL of pyridine and 150 mL of toluene in a 3-neck round bottom flask equipped with a stir bar, reflux condenser, and temperature probe. The heterogeneous solution was heated to reflux (110° C.). The solution became homogeneous during the initial temperature increase to 110° C. After a total of 16 hours at 110° C., the heating was discontinued and the reaction was allowed to cool to room temperature. Concentration of the heterogeneous solution under reduced pressure yielded a solid off-white product 18. The diol was synthesized in 78% yield (15.4 g).

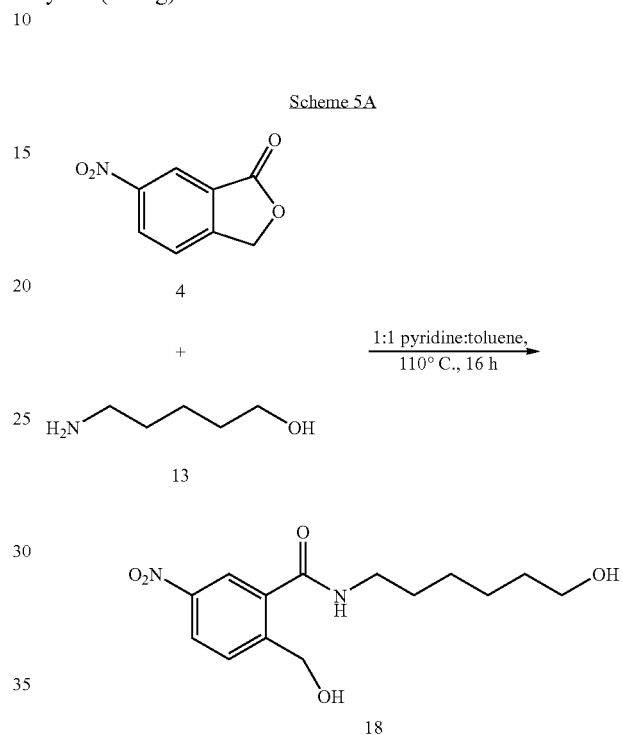

Step 2:

As shown below in Scheme 5B, The product from step one 18 (azeotroped 3×75 mL with pyridine) was dissolved in 200 mL of pyridine. Dimethoxytrityl chloride (ChemGenes RN-1401) (15.8 g, 0.0468 mol) was added in 4 portions over 1 hour. The reaction was stirred under argon overnight. The reaction was quenched with 5 mL of methanol and concentrated to a paste. The paste was then dissolved in DCM (200 mL) and the organic layer washed with water (1×100 mL), cold 10% citric acid (2×100 mL), and brine (1×100 mL). The organic layer was dried over MgSO₄ and filtered. Column chromatography in 1:2 DCM:methanol separated the regioisomers 19 and 20. The protection and isolation yielded 5.4 g (35%) of alcohol 19.

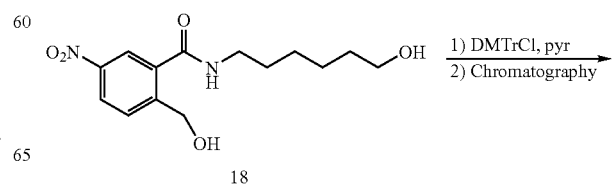

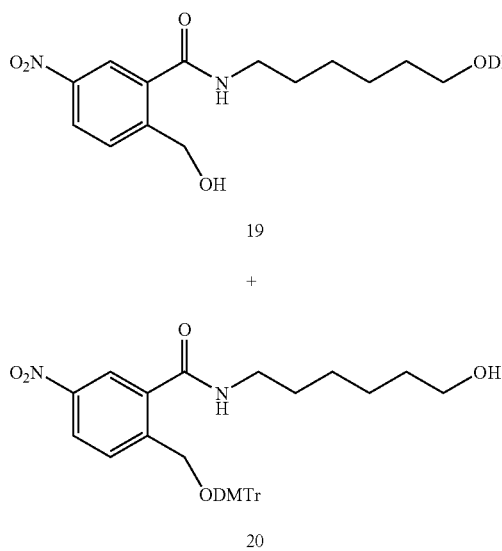

19

+

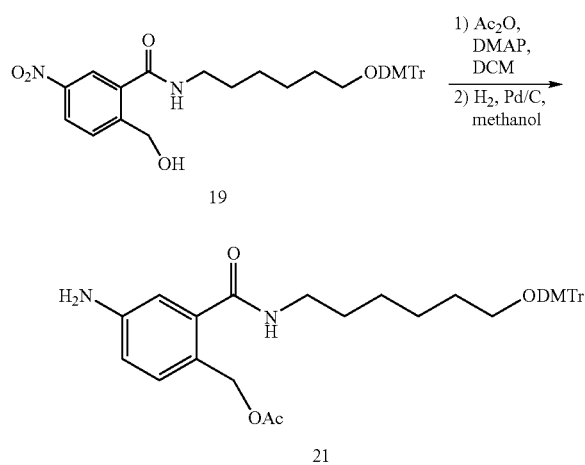

20

Step 3:

As shown in Scheme 5C, benzylic alcohol 19 (5.0 g, 0.008 mol) was dissolved in DCM (70 mL) and 1.5 equivalents of dimethylaminopyridine (DMAP) (1.5 g) was added followed by addition of 1 mL of acetic anhydride. After stirring for 1 hour at room temperature the mixture was diluted with DCM (100 mL), and washed with cold 10% citric acid (2×100 mL). The organic layer was dried over $MgSO_4$ and evaporated to afford a yellow oil. The oil was dissolved in methanol and the nitro group was reduced by hydrogenation with palladium on carbon in methanol to give the product 21 in 30% overall yield (4.6 g).

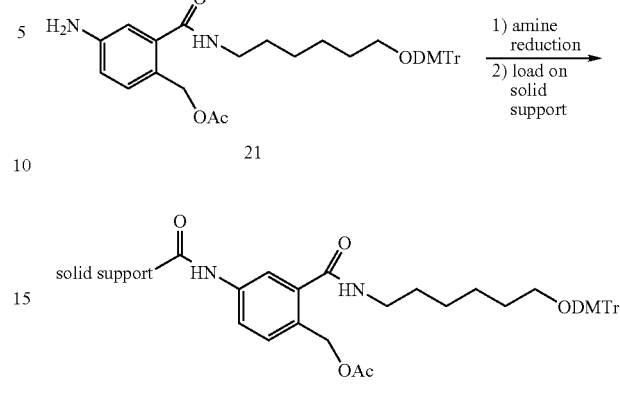

As shown in Scheme 5D, the primary amine group of the product 21 was then coupled to a commercially available solid support derivatized with a carboxylic acid to form the solid support reagent 22 (Solid Support Reagent 2).

Example 6

The following oligonucleotide: "agccuggggac-ccauggggggcut" (SEQ ID NO: 3), was synthesized, on a 1 μmol scale, on the following solid support reagents:

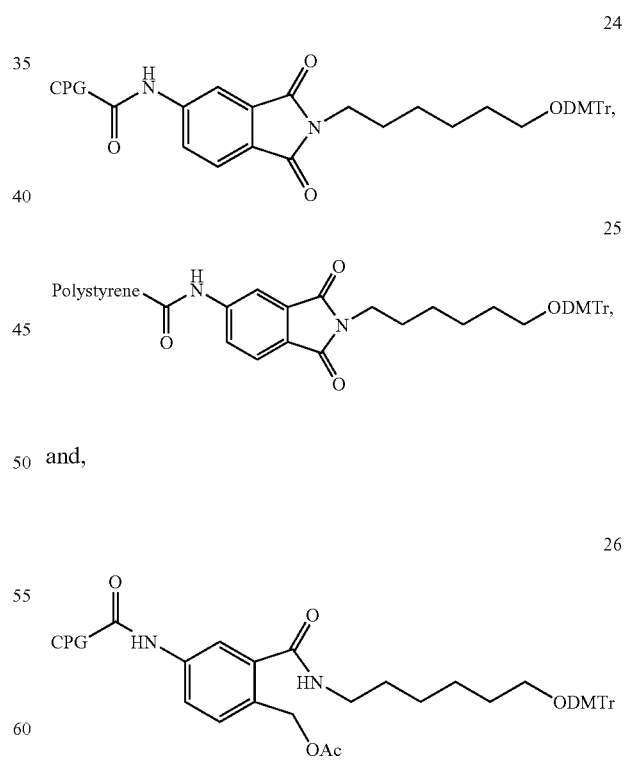

and,

In addition, this same oligonucleotide was synthesized, on a 1 μmol scale, on the following solid support reagent described in U.S. Pat. Nos. 5,419,966, the "966 reagent" (23), (herein incorporated by reference):

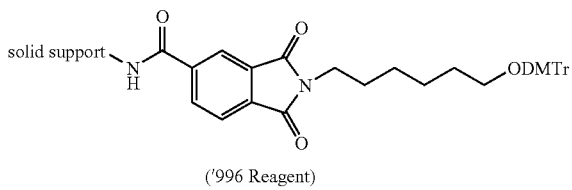

('996 Reagent)

Once this oligonucleotide was synthesized on 23, 24, and 26; each of these oligonucleotide linked solid support reagents was transferred to a glass vial and diluted with 1 mL of 40% aqueous methylamine. The vials were then placed in a heating block and deprotected at the given times and temperatures. After deprotection, vials were cooled in ice and diluted with 1 mL of 1:1 ethanol:water, filtered through a 0.45 μm syringe filter and evaporated to dryness on a speed vac. Pellets were dissolved in water and analyzed by SAX HPLC, and quantified by absorbance at 260 nm. Results are shown in Table 1. The standard error for quantitation of percentage of full length product (% FLP), in this assay, is 5%.

TABLE 1

| Solid Support Reagent | Temperature (° C.) | Time (min) | Yield (nmol) | % FLP |
|---|---|---|---|---|
| '966 Reagent (23) | 65 | 20 | 321 | 61 |
| SSR 1 (24) | 65 | 20 | 318 | 63 |
| '966 Reagent (23) | 45 | 120 | 269 | 65 |
| SSR 1 (24) | 45 | 120 | 313 | 61 |
| SSR 2 (26) | 45 | 60 | 308 | 66 |

These data, at 45° C., show the oligonucleotide yield using SSR 1 24 was approximately 15% greater than the oligonucleotide yield observed using 23 (under the same reaction conditions and with no statistically different percentage of full length product). Moreover, it should be noted that, at 45° C., SSR 2 26 also demonstrated, in half the reaction time, an approximately 15% greater yield as compared to the oligonucleotide yield observed using the '966 Reagent 23 at the same temperature. These data are significant given: i) the high cost of synthesizing many oligonucleotides and, ii) the decomposition observed in many oligonucleotides at higher temperatures (i.e., 65° C.).

We claim:

1. A compound according to Formula II:

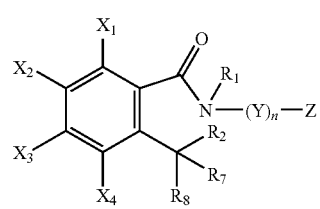

(II)

wherein
R$_1$ is selected from hydrogen and C$_1$-C$_6$ alkyl;
R$_2$ is selected from hydrogen, hydroxy, OC(O)CH$_3$, C$_1$-C$_6$ alkoxy, and C$_1$-C$_6$ alkyl, or together R$_1$ and R$_2$ form a single bond;
R$_7$ and R$_8$ are each independently selected from hydroxy, halogen, hydrogen, C$_1$-C$_6$ alkoxy, and OC(O)CH$_3$, or together R$_7$ and R$_8$ form a carbonyl;
X$_1$, X$_3$, and X$_4$ are selected from hydrogen, halogen, nitro, and amino;
X$_2$ is selected from nitro, —NH$_2$, alkylamino, and dialkylamino;
Y is methylene;
n is 1, 2, 3, 4, 5, 6, 7, 8, 9, or 10;
Z is OR;
R is selected from hydrogen, SiR$^a$R$^b$R$^c$, CR$^a$R$^b$R$^c$, heteroalkyl, and C$_1$-C$_6$ alkyl;
R$^a$, R$^b$, and R$^c$ are the same as or different from each other and each represents methyl, ethyl, i-propyl, t-butyl, phenyl or substituted phenyl.

2. The compound of claim 1, wherein together R$_7$ and R$_8$ form a carbonyl.

3. The compound of claim 1, wherein together R$_1$ and R$_2$ form a single bond.

4. The compound of claim 1, wherein R$_1$ is hydrogen.

5. The compound of claim 1, wherein one of R$_7$ or R$_8$ is OC(O)CH$_3$ and the other is hydrogen.

6. The compound of claim 1, wherein one of R$_7$ or R$_8$ is hydroxy and the other is hydrogen.

7. The compound of claim 1, wherein X$_2$ is nitro.

8. The compound of claim 1, wherein n is 6.

9. The compound as in claim 1, wherein R is selected from hydrogen, Si(t-butyl)(CH$_3$)$_2$, and C(C$_6$H$_5$)(4-MeOC$_6$H$_4$)$_2$.

10. The compound of claim 1, wherein at least one of X$_1$, X$_3$, and X$_4$ is halogen.

11. The compound of claim 1, wherein R$_1$ and R$_2$ form a single bond; together R$_7$ and R$_8$ form a carbonyl; X$_1$, X$_3$, and X$_4$ are hydrogen; X$_2$ is —NH$_2$; Y is methylene; n is 6; and Z is OR, wherein, R is CR$^a$R$^b$R$^c$.

12. The compound, of claim 1, having the structure:

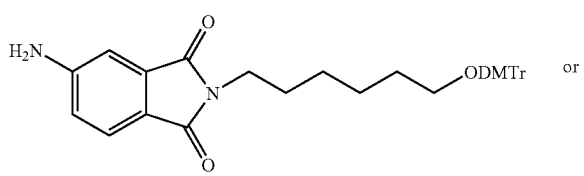

or

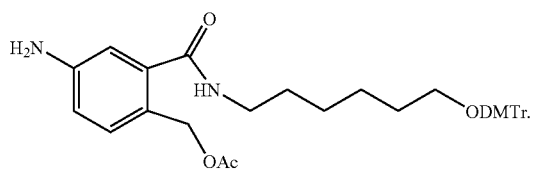

13. The compound of claim 1, wherein R$_1$ is hydrogen; R$_2$ is OC(O)CH$_3$; R$_7$ and R$_8$ are hydrogen; X$_1$, X$_3$, and X$_4$ are hydrogen; X$_2$ is NH$_2$; Y is methylene; and n is 6; Z is OR, wherein, R is CR$^a$R$^b$R$^c$.

14. A compound having the following Formula IV:

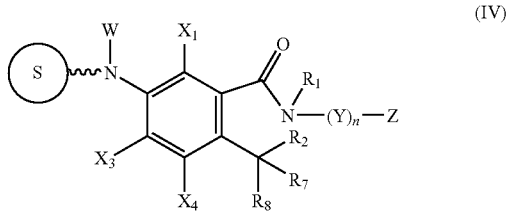

(IV)

wherein

is a solid support;
the wavy line ∿∿∿ represents a carbon chain which optionally contains a carbonyl;
W is selected from hydrogen and $C_1$-$C_6$ alkyl;
$R_1$ is selected from hydrogen and $C_1$-$C_6$ alkyl;
$R_2$ is selected from hydrogen, hydroxy, $OC(O)CH_3$, $C_1$-$C_6$ alkoxy, and $C_1$-$C_6$ alkyl, or together $R_1$ and $R_2$ form a single bond;
$R_7$ and $R_8$ are each independently selected from hydroxy, halogen, hydrogen, $C_1$-$C_6$ alkoxy, and $OC(O)CH_3$, or together $R_7$ and $R_8$ form a carbonyl;
$X_1$, $X_3$ and $X_4$ are selected from hydrogen, halogen, nitro, and amino;
Y is methylene; and
n is selected from 1, 2, 3, 4, 5, 6, 7, 8, 9, and 10;
Z is OR;
R is selected from hydrogen, $SiR^aR^bR^c$, $CR^aR^bR^c$, heteroaryl, and $C_1$-$C_6$ alkyl;
$R^a$, $R^b$, and $R^c$ are the same as or different from each other and each represents methyl, ethyl, i-propyl, t-butyl, phenyl or substituted phenyl.

15. The compound of claim 14, wherein the solid support is selected from controlled pore glass (CPG), styrene-divinylbenzene (DVB) co-polymer, polyethylene glycol (PEG) and methacrylate based polymer.

16. The compound of claim 14, wherein the carbon chain is a carbonyl.

17. The compound of claim 16, wherein $R_1$ and $R_2$ form a single bond; $R_7$ and $R_8$ form a carbonyl; $X_1$, $X_3$, and $X_4$ are hydrogen; W is a hydrogen; Y is methylene; n is 6; and Z is OR, wherein, R is $CR^aR^bR^c$.

18. The compound of claim 16, wherein $R_1$ is hydrogen; $R_2$ is an $OC(O)CH_3$; $R_7$ and $R_8$ are hydrogen; $X_1$, $X_3$, and $X_4$ are hydrogen; W is a hydrogen; Y is methylene; n is 6; and Z is OR, wherein, R is $CR^aR^bR^c$.

19. The compound of claim 14, having the structure:

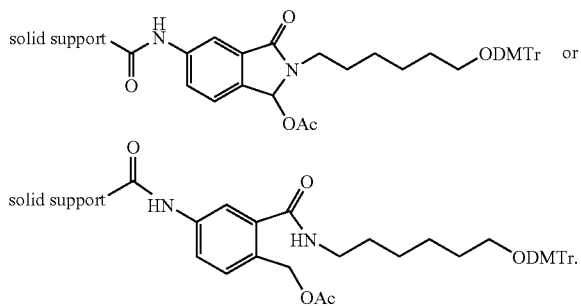

* * * * *

UNITED STATES PATENT AND TRADEMARK OFFICE
CERTIFICATE OF CORRECTION

PATENT NO. : 8,362,234 B2  Page 1 of 1
APPLICATION NO. : 12/225568
DATED : January 29, 2013
INVENTOR(S) : Paul Hatala et al.

It is certified that error appears in the above-identified patent and that said Letters Patent is hereby corrected as shown below:

Claim 19, at column 34, lines 20 to 26, the formula should appear as follows:

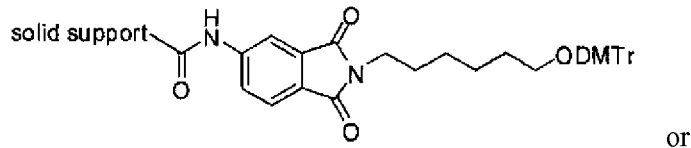

or

Signed and Sealed this
Twelfth Day of March, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,362,234 B2  
APPLICATION NO. : 12/225568  
DATED : January 29, 2013  
INVENTOR(S) : Hatala et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1073 days.

Signed and Sealed this
Seventeenth Day of September, 2013

Teresa Stanek Rea
*Deputy Director of the United States Patent and Trademark Office*